US008952005B2

(12) United States Patent
Layton et al.

(10) Patent No.: US 8,952,005 B2
(45) Date of Patent: Feb. 10, 2015

(54) SUBSTITUTED 1,3-BENZOTHIAZOL-2(3H)-ONES AND [1,3]THIAZOLO[5,4-B]PYRIDIN-2(1H)-ONES AS POSITIVE ALLOSTERIC MODULATORS OF MGLUR2

(71) Applicant: Merck Sharp & Dohme Corp., Rahway, NJ (US)

(72) Inventors: Mark E. Layton, Harleysville, PA (US); Michael J. Kelly, III, Wayne, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/048,608

(22) Filed: Oct. 8, 2013

(65) Prior Publication Data
US 2014/0045829 A1 Feb. 13, 2014

Related U.S. Application Data

(63) Continuation of application No. 13/641,780, filed as application No. PCT/US2011/033716 on Apr. 25, 2011, now abandoned.

(60) Provisional application No. 61/329,344, filed on Apr. 29, 2010.

(51) Int. Cl.
*A61K 31/54* (2006.01)
*C07D 261/20* (2006.01)

(52) U.S. Cl.
USPC ............ 514/228.5; 514/233.8; 514/321; 514/338; 544/58.6; 544/135; 546/198; 546/270.1; 548/159; 548/165

(58) Field of Classification Search
USPC .......... 514/228.5, 233.8, 321, 338; 544/58.6, 544/135; 548/159, 165; 546/198, 270.1
See application file for complete search history.

(56) References Cited

U.S. PATENT DOCUMENTS

| | | | |
|---|---|---|---|
| 7,799,782 B2 * | 9/2010 | Munson et al. | 514/234.5 |
| 8,686,008 B2 * | 4/2014 | McCurdy et al. | 514/367 |
| 2004/0044258 A1 | 3/2004 | Shoda et al. | |
| 2007/0213323 A1 | 9/2007 | Imogai et al. | |
| 2010/0075994 A1 | 3/2010 | Cao et al. | |

FOREIGN PATENT DOCUMENTS

EP 0022317 1/1981

OTHER PUBLICATIONS

McCurdy et al. CAS: 154: 101862, 2010.*
Ebrahimzadeh et al. CAS: 153: 497317, 2010.*
Perzborn's CAS: 148: 538247, 2008.*
Poupaeert et al. et al. CAS: 137: 201281, 2002.*
McDonald et al., "Physiological and Pathophysiological Roles of Excitatory Amino Acids During Central Nervous System Development", Brain Research Reviews, vol. 15, pp. 41, 1990.
Ozawa et al., "Glutamate Receptors in the Mammalian Central Nervous System", Prog. Neurbio, ol. 54, pp. 581, 1998.
Oswald et al., "Structure of Glutamate Receptors", Current Drug Targets, vol. 87, pp. 573-582, 2007.
Schoepp et al., "3,5-Dihydroxypehenylglycine is a highly Selective Agonist for Phosphoinositide-Linked metabotropic Glutamate Receptors in the Rat Hoppocampus", J. Neurochem, vol. 63, pp. 769, 1994.
Ito et al., "3,5-Dihyroxyphenyl-glycine: A Potent Agonist of Metabotropic Glutamate Receptors", Keurep, vol. 3, pp. 1013, 1992.
Monn et al., "Design, Synthesis, and Pharmalogical Characterization of (+)-2-Aminobicyclo[3.1.0] Hexane 2,6-Dicarboxylic Acid (LY35-4749): A Potent Selective, and Orally Active Group 2 Metabotropic Glutamate Receptor Agaonist Possessing Anticonvulsant and Anxiolytic Properties", J. Med. Chem, vol. 40, pp. 528, 1997.
Schoepp et al., "LY354740 is a Potent and Highly Selective Goup II Metabotropic Glutamate Receptor Agonist in Cells Expressing Human Glutamate Receptors"Neuropharmacol., vol. 36, pp. 1, 1997.
Cartmell et al., "Regulation of Neurotransmitter Release by Metabotropic Glutamate Receptors", Neurochem 75, pp. 889, 2000.
Schoepp, "Novel Functions for Subtypes of Metabotropic Glutamate Receptors", Neurochem Int, vol. 24, pp. 439, 1994.
Nakazato et al, "Synthesis, SARs, and Pharmacological Characterization of 2-Amino-3 or 6-fluorobicyclo[3.1.0]hexane-2,6-dicarboxylic Acid Derivatives as Potent, Selective, and Orally Active Group II Metabotropic Glutamate Receptor Agonists", J. Med. Chem, vol. 43, pp. 4893, 2000.
Patil et al., "Activation of mGlu2/3 Receptors as a New Approach to Treat Schizophrenia: A Randomized Phase 2 Clinical Trial", Nature Medicine, vol. 13, pp. 1102, 2007.
Galici et al. , "A Selective Allosteric Potentiator of Metabotropic Glutamate (mGlu) 2 Receptors has Effects Similar to an Orthosteric mGlu2/3 Receptor Agonist in Mouse Models Predictive of Antipsychotic Activity", J. of Pharmacology and Experimental Therapeutics, vol. 325, pp. 1181, 2005.
Johnson et al., "Discovery of Allosteric Potentiators for the Metabotropic glutatmate 2 Receptor: Synthesis and Subtype Selectivity of N-(4-(2-Methoxypehnoxy)phenyl)-N-(2,22,-Trifluoroethylsulfonyl) ", Med. Chem, vol. 46, pp. 3189, 2003.
Pinkerton et al., "Phenyl-Tetrazolyl Acetophenones: Discovery of Positiive Allosteric Potentiators for the Metabotropic Glutamate 2 Receptor"J. Med. Chem, vol. 47, pp. 4595, 2004.

(Continued)

*Primary Examiner* — Rei-tsang Shiao
(74) *Attorney, Agent, or Firm* — Keith D. MacMillan; John C. Todaro

(57) ABSTRACT

The present invention is directed to benzothiazol-one and thiazolo pyridine-one derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

14 Claims, No Drawings

(56) References Cited

OTHER PUBLICATIONS

Johnson et al., "Allosteric Modulators of Metabotropic Glutamate Receptors: Lessons learnt from mGlu1, mGlu2 and mGlu5 Potentiators and Antagonists", Biochemical Soc. Trans 32, pp. 881, 2004.
Monaghan et al., "The Excitatory Aminio Acid Receptors: Their Classes, Pharmacology, and Distinct Properties in the Function of the Central Nervous System", Ann. Rev. Pharmcol. Toxicol, vol. 29, pp. 365-402, 1989.
Schoepp et al., "Metabotropic Glutamate Receptors and Neuronal Degenerative Disorders", Neurobio Aging, vol. 15, pp. 261-263, 1994.
Meldrum et al., "Excitatory Amino Acid Neurotoxicity and Neurodegenerative Disease", Tr. Pharmacol. Sci., vol. 11, pp. 379-387, 1990.

* cited by examiner

SUBSTITUTED 1,3-BENZOTHIAZOL-2(3H)-ONES AND [1,3]THIAZOLO[5,4-B]PYRIDIN-2(1H)-ONES AS POSITIVE ALLOSTERIC MODULATORS OF MGLUR2

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGlu5R, are known to activate phospholipase C (PLC) via Gαq-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of Gαi-protein. These receptors can be activated by a selective compound such as 1S,2S,SR,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activitation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via Gαi and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psychopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to benzothiazol-one and thiazolo pyridine-one derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The invention encompasses a genus of compounds of Formula I

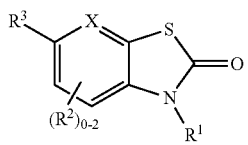

wherein:
$R^1$ is selected from the group consisting of:
(1) $C_{1-8}$alkyl,
(2) $(CHR)_pC_{5-10}$heterocyclyl,
(3) $(CHR)_pC_{6-10}$aryl,
(4) $(CHR)_pC_{3-6}$cycloalkyl, said alkyl, heterocyclyl, aryl, and cycloalkyl, optionally substituted with 1 to 3 groups of $R^a$;
X represents —$CR^b$—, or —N—;
each $R^2$ is independently selected from the group consisting of: hydrogen, halo, OH, $C_{1-4}$alkyl, $C_{1-4}$alkoxy, $CF_3$ and —CN;
$R^3$ is selected from the group consisting of: C(O)R, $C_{6-10}$ aryl and $C_{5-10}$ heterocyclyl, $OC_{6-10}$ aryl, $OC_{5-10}$ heterocyclyl wherein said aryl and heterocyclyl are optionally substituted with 1 to 3 substituents $R^a$;
each $R^a$ is independently selected from the group consisting of:
(1) halo,
(2) $C_{1-8}$alkyl,
(3) $C_{2-6}$alkenyl,
(4) $C_{2-6}$alkynyl,
(5) $C_{3-6}$cycloalkyl,
(6) $C_{1-6}$alkoxy,
(7) $C_{3-6}$cycloalkoxy,
(8) —CN,
(9) —OH,
(10) —C(O)—O—R,
(11) —C(O)—$C_{1-6}$alkyl,
(12) —N(R)$_2$,
(13) —C(O)—N(R)$_2$,
(14) —S(O)$_k$—$C_{1-6}$alkyl, wherein k is 0, 1 or 2,
(15) —$(CH_2)pC_{6-10}$aryl,
(16) —$(CH_2)pC_{5-10}$heterocyclyl,
(17) $CF_3$,
(18) —C(O)-aryl,
(19) —N(R)-aryl,
(20) benzyl,
(21) benzyloxy,
(22) phenoxy,
(23) —C(CH$_3$)$_2$OR,
(24) —SH,
(25) —SO$_2$N(R)R,
(26) —$(CH_2)_pN(R)C(O)N(R)R$,
(27) —$(CH_2)pN(R)C(O)C_{1-6}$alkyl,
(28) —$(CH_2)pN(R)SO_2N(R)R$, and
(29) —B(OH)$_2$,
(30) —OR,
(31) —$(CH_2)_pNHC(O)OC_{1-6}$alkyl,
(32) —$OC_{5-10}$heterocyclyl, wherein groups (2) to (7), (11), (14) to (16), (18) to (23), and (32) above are optionally substituted with one up to the maximum number of substitutable positions of one or more substituents independently selected from the group consisting of: OH, CN, halo, carboxy, —C(O)—O—$C_{1-4}$alkyl, $C_{1-4}$alkyl, $C_{1-4}$alkoxy, $C_{1-4}$alkylamino, phenyl and C5-10 heterocycle,
R is selected from the group consisting of: H, $(CH_2)_pC_{6-10}$aryl and $C_{1-6}$alkyl;
$R^b$ and $R^k$ independently represent H or halo;
p represents 0-4;
and pharmaceutically acceptable salts thereof.

Within the sub-genus the invention encompasses a first class of compounds of Formula I wherein p is 0-2, 0-1, 1, or 0.

Within the sub-genus, the invention encompasses a second class of compounds of Formula I wherein $R^a$ is selected from the group consisting of: halo, $C_{1-8}$alkyl, $C_{3-6}$cycloalkyl, —$OC_{5-10}$heterocyclyl, $C_{1-6}$alkoxy, $C_{3-6}$cycloalkoxy, —CN, —OH, —C(O)—$C_{1-6}$alkyl, —$(CH_2)pC_{6-10}$aryl, —$(CH_2)pC_{5-10}$heterocyclyl, $CF_3$, —C(O)-aryl, and —$(CH_2)pNHC(O)OC_{1-6}$alkyl, said alkyl, aryl and heterocyclyl optionally substituted with 1 to 3 groups of OH, CN, halo, carboxy, —C(O)—O—$C_{1-4}$alkyl, $C_{1-4}$alkyl, $C_{1-4}$alkoxy, $C_{1-4}$alkylamino, phenyl and $C_{5-10}$ heterocycle.

Within the sub-genus, the invention encompasses a third class of compounds of Formula I wherein $R^1$ is $(CHR)pC_{3-6}$cycloalkyl, —$(CH_2)_p$piperidinyl, $(CH_2)_p$phenyl, and $C_{1-6}$ alkyl, said cycloalkyl, piperidinyl, phenyl and alkyl optionally substituted with 1 to 3 groups of $R^a$. Another sub-genus of this third class is realized when $R^1$ is optionally substituted $(CHR)pC_{3-6}$cycloalkyl. A further sub-genus of this third class is realized when $R^1$ is —(CH$_2$)pcyclopropyl, said cyclopropyl optionally substituted with 0-2 groups of halo. A further sub-genus of this third class is realized when the cyclopropyl is unsubstituted or substituted with 1-2 groups of halo, preferably fluoro. Still another sub-genus of this third class is realized when $R^1$ is optionally substituted $C_{1-6}$ alkyl. Still another sub-genus of this third class is realized when $R^1$ is optionally substituted $(CH_2)_p$phenyl.

Also within the sub-genus, the invention encompasses a fourth class of compounds of Formula I wherein $R^2$ is hydrogen or halogen.

Also within the sub-genus, the invention encompasses a fifth class of compounds of Formula I wherein $R^3$ is $C_{6-10}$ aryl, $C_{5-10}$ heterocyclyl, $OC_{6-10}$ aryl or $OC_{5-10}$ heterocyclyl optionally substituted with 1 to 3 substituents $R^a$. Another sub-genus of this fifth class is realized when $R^3$ is selected from the group consisting of phenyl, pyridyl, benzfuranyl, pyrazinyl, pyrimidinyl, O-phenyl, or O-pyridyl all of which optionally substituted with 1 to 3 groups of $R^a$. Another sub-genus of this fifth class is realized when $R^3$ is optionally substituted phenyl. Still another sub-genus of this fifth class is realized when $R^3$ is optionally substituted pyridyl. Still another sub-genus of this fifth class is realized when $R^3$ is optionally substituted pyrimidinyl. A further sub-genus of this fifth class is realized when $R^3$ is optionally substituted O-phenyl. Yet another sub-genus of this fifth class is realized when $R^3$ is optionally substituted O-pyridyl.

Also within the sub-genus, the invention encompasses a sixth class of compounds having Formula Ia

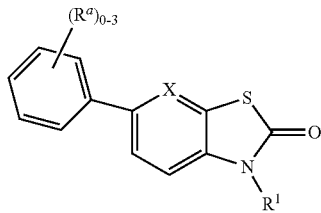

wherein X is —CH— or —N, $R^1$ is selected from —(CH$_2$)$_p$cyclopropyl, —(CH$_2$)$_p$cyclopentyl, —(CH$_2$)$_p$cyclohexyl, —(CH$_2$)$_p$piperidinyl, (CH$_2$)$_p$phenyl, and $C_{1-6}$ alkyl, said cyclopropyl, cyclopentyl, cyclohexyl and alkyl optionally substituted with 1-3 halo, $C_{1-6}$ alkyl, $CF_3$, —C(O)OC$_{1-6}$ alkyl, pyrimidinyl, 2,2-dimethylpropyl and 4,4,4-trifluorobutyl; and pharmaceutically acceptable salts thereof and $R^a$ is selected from the group consisting of CN, halo, OR, $CF_3$, —C(CH$_3$)$_2$OR, C1-6 alkyl, (CH$_2$)$_p$morpholinyl, (CH$_2$)$_p$dioxidomorpholinyl, and (CH$_2$)$_p$NHC(O)OC(CH$_3$)$_3$. A further sub-genus of the sixth class of compounds is realized when $R^1$ is —(CH$_2$)$_p$cyclopropyl optionally substituted with 1-2 halo, preferably the cyclopropyl is substituted with 1-2 fluoro and X is —CH—. A further sub-genus of the sixth class of compounds is realized when $R^1$ is —(CH$_2$)$_p$cyclopropyl optionally substituted with 1-2 halo, preferably the cyclopropyl is unsubstituted or substituted with 2 fluoro and X is —N—. Still another sub-genus of the sixth class of compounds is realized when $R^1$ is optionally substituted $C_{1-6}$ alkyl and X is —CH—. Still another sub-genus of the sixth class of compounds is realized when $R^1$ is optionally substituted $C_{1-6}$ alkyl and X is —N.

Also within the sub-genus, the invention encompasses a seventh class of compounds having Formula Ib

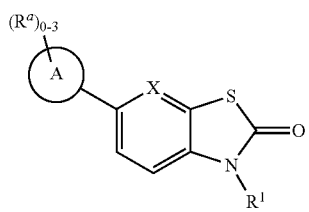

wherein X is —CH— or —N, A is pyridyl and $R^1$ is selected from —(CH$_2$)$_p$cyclopropyl, —(CH$_2$)$_p$cyclopentyl, —(CH$_2$)$_p$cyclohexyl, —(CH$_2$)$_p$piperidinyl, (CH$_2$)$_p$phenyl, and $C_{1-6}$ alkyl, said cyclopropyl, cyclopentyl, cyclohexyl and alkyl optionally substituted with 1-3 halo, $C_{1-6}$ alkyl, $CF_3$, —C(O)OC$_{1-6}$ alkyl, pyrimidinyl, 2,2-dimethylpropyl and 4,4,4-trifluorobutyl; and pharmaceutically acceptable salts thereof and $R^a$ is selected from the group consisting of CN, halo, OR, $CF_3$, —C(CH$_3$)$_2$OR, C1-6 alkyl, (CH$_2$)$_p$morpholinyl, (CH$_2$)$_p$dioxidomorpholinyl, and (CH$_2$)$_p$NHC(O)OC(CH$_3$)$_3$. A further sub-genus of the seventh class of compounds is realized when $R^1$ is —(CH$_2$)$_p$cyclopropyl optionally substituted with 1-2 halo, preferably the cyclopropyl is unsubstituted or substituted with 2 fluoro and X is —CH—. A further sub-genus of the seventh class of compounds is realized when $R^1$ is —(CH$_2$)$_p$cyclopropyl optionally substituted with 1-2 halo, preferably the cyclopropyl is unsubstituted or substituted with 2 fluoro and X is —N. Still another sub-genus of the seventh class of compounds is realized when $R^1$ is optionally substituted $C_{1-6}$ alkyl and X is —CH—. Still another sub-genus of the seventh class of compounds is realized when $R^1$ is optionally substituted $C_{1-6}$ alkyl and X is —N.

Also within the sub-genus, the invention encompasses an eighth class of compounds having Formula Ic

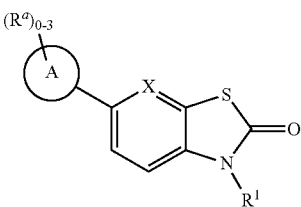

wherein X is —CH— or —N, A is O-phenyl or O-pyridyl and $R^1$ is selected from —(CH$_2$)$_p$cyclopropyl, —(CH$_2$)$_p$cyclopentyl, —(CH$_2$)$_p$cyclohexyl, —(CH$_2$)$_p$piperidinyl, (CH$_2$)$_p$phenyl, and $C_{1-6}$ alkyl, said cyclopropyl, cyclopentyl, cyclohexyl and alkyl optionally substituted with 1-3 halo, $C_{1-6}$ alkyl, $CF_3$, —C(O)OC$_{1-6}$ alkyl, pyrimidinyl, 2,2-dimethylpropyl and 4,4,4-trifluorobutyl; and pharmaceutically acceptable salts thereof and $R^a$ is selected from the group consisting of CN, halo, OR, $CF_3$, —C(CH$_3$)$_2$OR, C1-6 alkyl, (CH$_2$)$_p$morpholinyl, (CH$_2$)$_p$dioxidomorpholinyl, and (CH$_2$)$_p$NHC(O)OC(CH$_3$)$_3$. Another sub-genus of the eighth class of compounds is realized when $R^1$ is —(CH$_2$)$_p$cyclopropyl optionally substituted with 1-2 halo, preferably the cyclopropyl is unsubstituted or substituted with 2 fluoro and X is —CH—. A further sub-genus of the eighth class of compounds is realized when $R^1$ is —(CH$_2$)$_p$cyclopropyl optionally substituted with 1-2 halo, preferably the cyclopropyl is unsubstituted or substituted with 2 fluoro and X is —N. Still another sub-genus of the eighth class of compounds is realized when $R^1$ is optionally substituted $C_{1-6}$ alkyl and X is —CH—. Still another sub-genus of the eighth class of compounds is realized when $R^1$ is optionally substituted $C_{1-6}$ alkyl and X is —N. A further sub-genus of the eighth class of compounds is realized when X is —CH—, A is optionally substituted O-phenyl, and $R^1$ is selected from optionally substituted —(CH$_2$)$_p$cyclopropyl. A still further sub-genus of the eighth class of compounds is realized when X is —CH—, A is optionally substituted O-pyridyl, and $R^1$ is selected from optionally substituted —(CH$_2$)$_p$cyclopropyl. A further sub-genus of the eighth class of compounds is realized when X is —N—, A is optionally substituted O-phenyl, and $R^1$ is selected from optionally substituted —(CH$_2$)$_p$cyclopropyl. A still further sub-genus of the eighth class of compounds is realized when X is —N—, A is optionally substituted O-pyridyl, and $R^1$ is selected from optionally substituted —(CH$_2$)$_p$cyclopropyl.

The invention also encompasses a pharmaceutical composition comprising a compound of Formula I, Ia, Ib, or Ic in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formula I. The invention also encompasses this method wherein the neurological or psychiatric disorder associated with glutamate dysfunction is schizophrenia.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfinyl, arylsulfinyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" and "halo" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of mGluR2 modulator sufficient to inhibit or enhance the desired.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention are potentiators of metabotropic glutamate mGluR receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Exemplifying the invention are Examples 1-1 to 1-122, 2-1 to 2-42, 3-1 to 3-9 and 4-1 to 4-27, described herein. The subject compounds are useful in a method of potentiating metabotorpic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of metabotropic glutamate receptor activity, in particular mGluR2 activity, may be demonstrated by methodology known in the art. Inhibition constants are determined as follows. The compounds of the present invention may be tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr− cells stably expressing recombinant human mGluR2 and Gα16 loaded with Fluo-4 AM (Invitrogen, Carlsbad Calif.) are treated with dose responses of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonist or potentiation are plotted as dose responses and the curves are fitted with a four parameters logistic equation giving EC50 and Hill coefficient using the iterative non linear curve fitting software program.

The compounds of the present invention may also be tested in a $[^{35}S]$-GTPγS assay. The stimulation of $[^{35}S]$-GTPγS binding is a common functional assay to monitor Gαi-coupled receptor in native and recombinant receptor membrane preparation. Membrane from cells stably expressing hmGlu2 CHO-K1 (50 μg) are incubated in a 96 well plate for 1 hour in the presence of GTPγS$^{35}$ (0.05 nM), GDP (5 μM) and compounds. The reaction is stopped by rapid filtration over Unifilter GF/B plate (Packard, Bioscience, Meriden Conn.) using a 96-well cell harvester (Brandel Gaithersburg, Md.). The filter plates are counted using Topcount counter (Packard, Bioscience, Meriden Conn., USA). When compounds are evaluated as potentiators they are tested in the presence of glutamate (1 μM). The activation (agonist) or the potentiation of glutamate (potentiator) curves are fitted with a four parameters logistic equation giving $EC_{50}$ and Hill coefficient using the iterative non linear curve fitting software GraphPad (San Diego Calif., USA).

In particular, Examples 1-6 to 1-12, 2-3, 3-2 to 3-4, 4-2, 4-3, 5-2 to 5-29, 6-2 to 6-16, 7-2 to 7-5, 8-2, 8-3, 9-2 to 9-16, 10-2 to 10-7, 11-4, 12-1, 13-5, 14-1, 15-2, 16-3, 17-1, 18-3 to 18-11 and 19-1 were tested and demonstrated activity in potentiating the mGluR2 receptor in the FLIPR assay, generally with an $EC_{50}$ of less than about 3 μM. Examples 1-6 to 1-12, 2-3, 3-2 to 3-4, 4-2, 4-3, 5-2 to 5-29, 6-2 to 6-16, 7-2 to 7-5, 8-2, 8-3, 9-2 to 9-16, 10-2 to 10-7, 11-4, 12-1, 13-5, 14-1, 15-2, 16-3, 17-1, 18-3 to 18-11 and 19-1 resulted in a minimum 2.0-fold potentiation of glutamate response in the presence of an EC20 concentration of glutamate (900 nM). Such results are indicative of the intrinsic activity of the compounds in use as potentiators of mGluR2 receptor activity. Representative FLIPR $EC_{50}$ Values (Nanomolar Units)

| Ex.  | EC50 | N |
|------|------|---|
| 2-3  | 153  | 2 |
| 3-2  | 34   | 2 |
| 5-2  | 17   | 8 |
| 6-16 | 65   | 2 |
| 9-15 | 248  | 2 |
| 16-3 | 15   | 3 |
| 18-3 | 306  | 2 |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

In an embodiment the present invention provides a method for treating migraine, comprising: administering to a patient in need thereof an effective amount of a compound of formula I. In another embodiment the present invention provides a method for preventing or treating anxiety, comprising: administering to a patient in need thereof an effective amount of a compound of formula I. Particular anxiety disorders of the invention are generalized anxiety disorder, panic disorder, and obsessive compulsive disorder. In another embodiment the present invention provides a method for treating schizophrenia, comprising: administering to a patient in need thereof an effective amount of a compound of formula I. In yet another embodiment the present invention provides a method for treating epilepsy, comprising: administering to a patient in need thereof an effective amount of a compound of formula I.

In an embodiment, the present invention provides a method for the treatment of schizophrenia comprising: administering to a patient in need thereof an effective amount of a compound of formula I or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including migraine, and that these systems evolve with medical scientific progress Thus, in an embodiment the present invention provides a method for treating migraine, comprising: administering to a patient in need thereof an effective amount of a compound of formula I or a pharmaceutical composition thereof. In one of the available sources of diagnostic tools, Dorland's Medical Dictionary (23'd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder;

or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGluR agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form may be utilized containing such other drugs and the compound of Formula I. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be utilized. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein. The compounds of the present invention can be prepared in a variety of fashions.

All patents, publications and pending patent applications identified are hereby incorporated by reference.

Abbreviations used in the description of the chemistry and in the Examples that follow are: AcOH (acetic acid); Boc (tert-butyl carbamate); BSA (bovine serum albumin); Cbz-Cl (benzylchloroformate); CDCl$_3$ (chloroform-d); Cs2CO3 (cesium carbonate); CuOAc2 (copper (II) acetate); DCM (dichloromethane); DIAD (diisopropyl (E)-diazene-1,2-dicarboxylate); DIPEA (diisopropylethylamine); DMBA (1,3-dimethylbarbituric acid); DMF (N,N-dimethylformamide); DMSO (dimethyl sulfoxide); DTT (dithiothreitol); EDTA (ethylene-diamine-tetra-acetic acid); EGTA (ethylene-glycol-tetra-acetic acid); Et$_2$O (diethylether); EtOAc (ethyl acetate); EtOH (ethanol); HCl (hydrochloric acid); Hex (hexane); H2O2 (hydrogen peroxide); HOAc (acetic acid); HPLC (high-performance liquid chromatography); HRMS (high resolution mass spectrum); IPA (isopropanol); KI (potassium iodide); K2CO3 (potassium carbonate); KOAc (potassium acetate); LCMS (liquid chromatograph-mass spectrometer); LRMS (low resolution mass spectrum); MeI (methyl iodide); MeMgBr (methylmagnesium bromide); MeOH (methanol); NaHCO$_3$ (sodium bicarbonate); NaNO2 (sodium nitrite); NaOMe (sodium methoxide); Na$_2$SO$_4$ (sodium sulfate); Na2S2O3 (sodium thiosulfate); NMP (1-methyl-2-pyrrolidinone); NMR (nuclear magnetic resonance); Pd(dppf)Cl2 ([1,1'-bis(diphenylphosphino)ferrocene]palladium dichloride); Pd[P(tBu3)2]2 (bis(tri-tert-butylphosphine) palladium); PPh$_3$ (triphenyl phosphine); p-TSA-H2O (4-methylbenzenesulfonic acid hydrate); PyrBr3 (pyridinium bromide perbromide); RT (room temperature); THF (tetrahydrofuran); and TFA (trifluoroacteic acid).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula A hereinabove.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially available or are readily prepared by one of ordinary skill in the art.

SCHEME 1

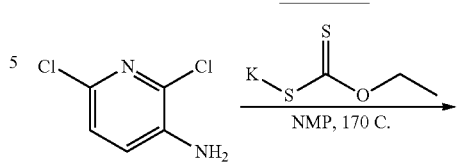

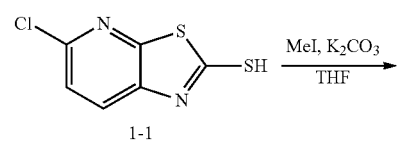

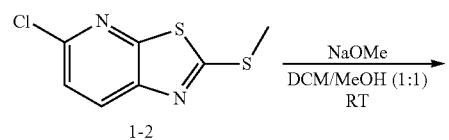

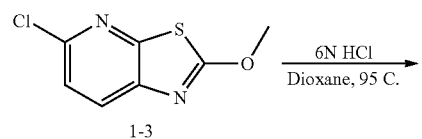

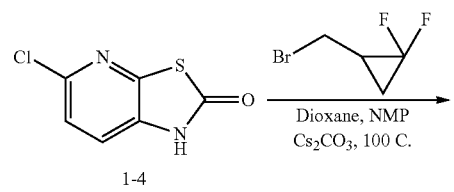

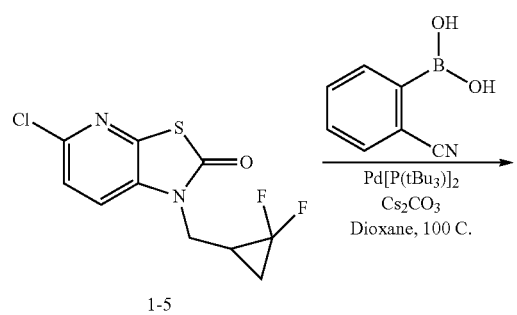

-continued

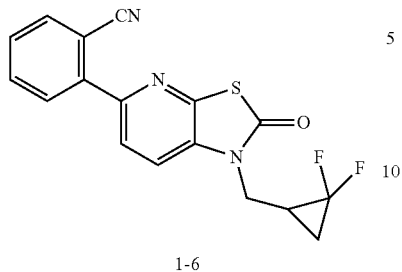

1-6

2-(1-{[2,2-difluorocyclopropyl]methyl}-2-oxo-1,2-dihydro[1,3]thiazolo[5,4-b]pyridin-5-yl)benzonitrile (1-6)

5-chloro[1,3]thiazolo[5,4-b]pyridine-2-thiol (1-1)

To a round bottom flask was added 2,6-dichloropyridin-3-amine (21.4 g, 131 mmol), potassium ethoxy(thioxo)methanethiolate (42.1 g, 262 mmol), and anhydrous NMP (300 mL). The reaction mixture was then heated to 170° C. while stirring in a hot oil bath with a water cooled reflux condenser attached under an atmosphere of nitrogen for 3.5 hours. The crude reaction mixture was then allowed to cool to room temperature, and acidified to pH 5 with glacial acetic acid, which led to a precipitate which was collected by filtration. This precipitate was then suspended in ethyl acetate and washed with water, then brine, dried over sodium sulfate, filtered, and concentrated to give 5-chloro[1,3]thiazolo[5,4-b]pyridine-2-thiol (1-1) as a tan solid. HRMS (M+H)$^+$: observed=202.9502, calculated=202.9499.

5-chloro-2-(methylthio)[1,3]thiazolo[5,4-b]pyridine (1-2)

To a round bottom flask was added 5-chloro[1,3]thiazolo[5,4-b]pyridine-2-thiol (1-1) (21.4 g, 106 mmol), anhydrous THF (400 mL), potassium carbonate (20.5 g, 148 mmol), followed by methyl iodide (16.9 g, 119 mmol). The reaction vessel was sealed and stirred at room temperature for 5 minutes. The crude reaction mixture was then suspended in ethyl acetate and washed with a saturated solution of sodium bicarbonate, followed by water, then brine, dried over sodium sulfate, filtered, and concentrated to give 5-chloro-2-(methylthio)[1,3]thiazolo[5,4-b]pyridine (1-2) as a pink solid. HRMS (M+H)$^+$: observed=216.9658, calculated=216.9655.

5-chloro-2-methoxy[1,3]thiazolo[5,4-b]pyridine (1-3)

To a round bottom flask was added 5-chloro-2-(methylthio)[1,3]thiazolo[5,4-b]pyridine (1-2) (11.5 g, 53.3 mmol), sodium methoxide (10.8 g, 200 mmol), anhydrous DCM (200 mL) and anhydrous MeOH (200 mL). The reaction mixture was then permitted to stir at room temperature under an atmosphere of nitrogen for 18 hours. The reaction mixture was then acidified to pH 5 with glacial acetic acid, then suspended in ethyl acetate and washed with water, then brine, dried over sodium sulfate, filtered, and concentrated. The resulting residue was purified by silica gel chromatography (0-6% IPA/DCM) to give 5-chloro-2-methoxy[1,3]thiazolo[5,4-b]pyridine (1-3) as an off-white solid. HRMS (M+H)$^+$: observed=198.9998, calculated=198.9994.

5-chloro[1,3]thiazolo[5,4-b]pyridin-2(1H)-one (1-4)

To round bottom flask was added give 5-chloro-2-methoxy [1,3]thiazolo[5,4-b]pyridine (1-3) (5.76 g, 28.7 mmol), 1,4-dioxane (90 mL), and a 6N solution of HCl in water (23.9 mL, 144 mmol). The reaction mixture was then heated to 95° C. while stirring in a hot oil bath with a water cooled reflux condenser attached under an atmosphere of nitrogen for 20 minutes. The crude reaction mixture was then allowed to cool to room temperature, diluted methanol and concentrated to give 5-chloro[1,3]thiazolo[5,4-b]pyridin-2(1H)-one (1-4) as a tan solid. HRMS (M+H)$^+$: observed=186.9731, calculated=186.9727.

5-chloro-1-[(2,2-difluorocyclopropyl)methyl][1,3]thiazolo[5,4-b]pyridin-2(1H)-one (1-5)

To a round bottom flask was added 5-chloro[1,3]thiazolo[5,4-b]pyridin-2(1H)-one (1-4) (3.5 g, 19 mmol), anhydrous NMP (30 mL), anhydrous 1,4-dioxane (60 mL), cesium carbonate (12 g, 37 mmol), followed by 2-(bromomethyl)-1,1-difluorocyclopropane (3.4 g, 20 mmol). The reaction mixture was then heated to 95° C. while stirring in a hot oil bath for 18 hours. The crude reaction mixture was then cooled to room temperature, then suspended in ethyl acetate and washed with a saturated solution of sodium bicarbonate, followed by water, then brine, dried over sodium sulfate, filtered, and concentrated. The resulting residue was purified by silica gel chromatography (0-40% EtOAc/Hex) to give 5-chloro-1-[(2,2-difluorocyclopropyl)methyl][1,3]thiazolo[5,4-b]pyridin-2(1H)-one (1-5) as a tan solid. HRMS (M+H)$^+$: observed=277.0008, calculated=277.0008.

2-(1-{[2,2-difluorocyclopropyl]methyl}-2-oxo-1,2-dihydro[1,3]thiazolo[5,4-b]pyridin-5-yl)benzonitrile (1-6)

To a microwave vial was added 5-chloro-1-[(2,2-difluorocyclopropyl)methyl][1,3]thiazolo[5,4-b]pyridin-2(1H)-one (1-5) (0.025 g, 0.090 mmol), (2-cyanophenyl)boronic acid (0.020 g, 0.14 mmol), cesium carbonate (0.059 g, 0.18 mmol), bis(tri-tert-butylphosphine) palladium (0.009 g, 0.02 mmol), 1,4-dioxane (1 mL), and water (0.2 mL). The reaction mixture was then heated under microwave irradiation at 100° C. for 10 minutes. The crude reaction mixture was then allowed to cool to room temperature, diluted with methanol, filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) gave 2-(1-{[2,2-difluorocyclopropyl]methyl}-2-oxo-1,2-dihydro [1,3]thiazolo[5,4-b]pyridin-5-yl)benzonitrile (1-6) as a brown solid. $^1$H NMR (400 MHz, CD$_3$OD): δ 7.87-7.72 (m, 5H); 7.60-7.54 (m, 1H); 4.25-4.10 (m, 2H); 2.23-2.15 (m, 1H); 1.61-1.54 (m, 1H); 1.38 (m, 1H). HRMS (M+H)$^+$: observed=344.0669, calculated=344.0664.

TABLE 1

The following compounds were prepared from 1-5 by a reaction sequence analogous to that illustrated in Scheme 1.

| Cmpd | Structure | IUPAC Name | Exact Mass [M + H]+ |
|---|---|---|---|
| 1-7 | 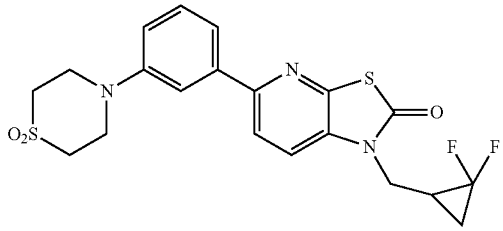 [SMILES: O=c1sc2nc(-c3cccc(N4CCS(=O)(=O)CC4)c3)ccc2n1CC1CC1(F)F] | 1-{[2,2-difluorocyclo-propyl]methyl}-5-[3-(1,1-dioxidothio morpholin-4-yl)phenyl][1,3]thiazolo[5,4-b]pyridin-2(1H)-one | Calc'd 452.0909, found 452.0927 |
| 1-8 | 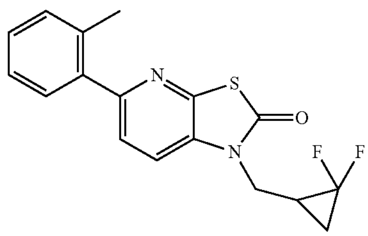 [SMILES: Cc1ccccc1-c1ccc2c(n1)sc(=O)n2CC1CC1(F)F] | 1-{[2,2-difluorocyclo-propyl]methyl}-5-(2-methylphenyl)[1,3]thiazolo[5,4-b]pyridin-2(1H)-one | Calc'd 333.0868, found 333.0865 |
| 1-9 | 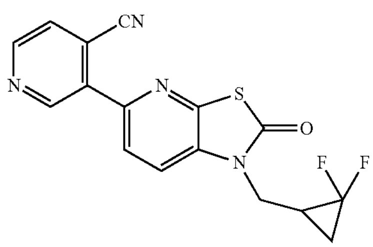 [SMILES: N#Cc1ccncc1-c1ccc2c(n1)sc(=O)n2CC1CC1(F)F] | 3-(1-{[2,2-difluorocyclo-propyl]methyl}-2-oxo-1,2-dihydro[1,3]thiazolo[5,4-b]pyridin-5-yl)pyridine-4-carbonitrile | Calc'd 345.0616, found 345.0616 |
| 1-10 | 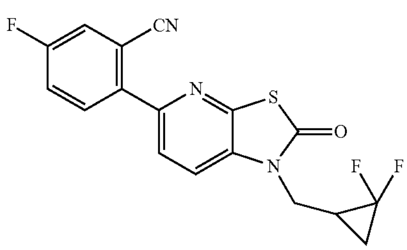 [SMILES: N#Cc1cc(F)ccc1-c1ccc2c(n1)sc(=O)n2CC1CC1(F)F] | 2-(1-{[2,2-difluorocyclo-propyl]methyl}-2-oxo-1,2-dihydro[1,3]thiazolo[5,4-b]pyridin-5-yl)-5-fluorobenzonitrile | Calc'd 362.0569, found 362.0570 |
| 1-11 | 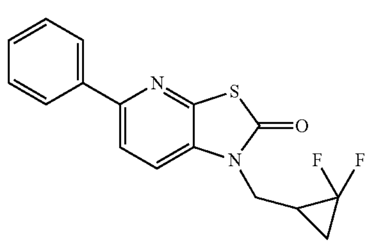 [SMILES: O=c1sc2nc(-c3ccccc3)ccc2n1CC1CC1(F)F] | 1-[(2,2-difluorocyclo-propyl)methyl]-5-phenyl[1,3]thiazolo[5,4-b]pyridin-2(1H)-one | Calc'd 319.0711, Found 319.0713 |

TABLE 1-continued

The following compounds were prepared from 1-5 by a reaction sequence analogous to that illustrated in Scheme 1.

| Cmpd | Structure | IUPAC Name | Exact Mass [M + H]+ |
|---|---|---|---|
| 1-12 | 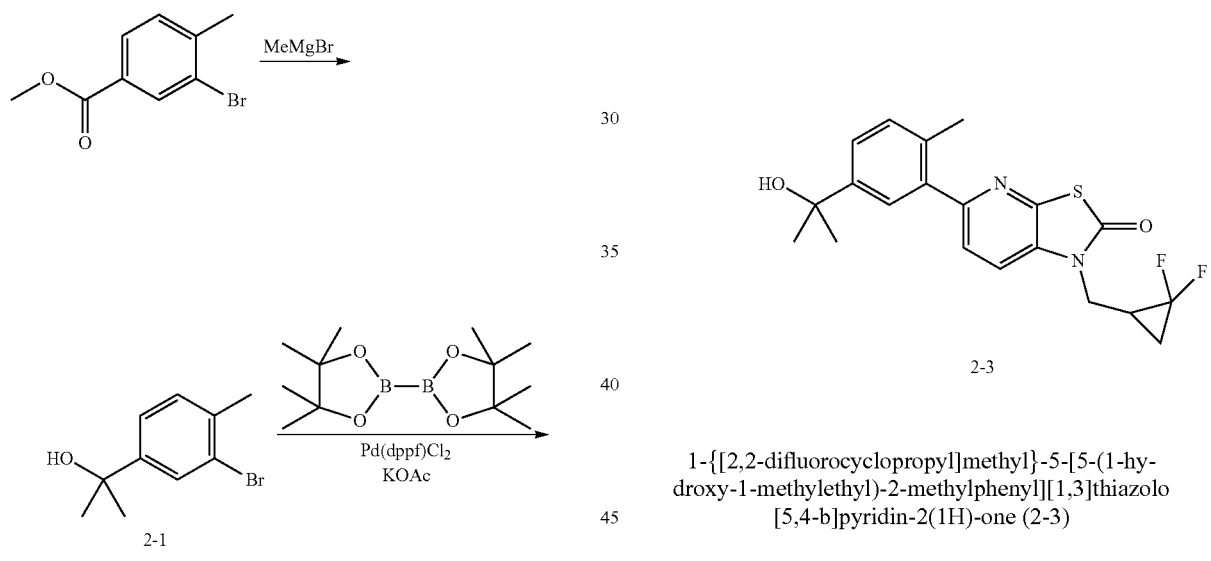 | 5-{5-[(4-acetylpiperazin-1-yl)methyl]-2-methyl-phenyl}-1-[(2,2-difluorocyclopropyl)methyl][1,3]thiazolo[5,4-b]pyridin-2(1H)-one | Calc'd 473.1817, Found 473.1833 |

SCHEME 2

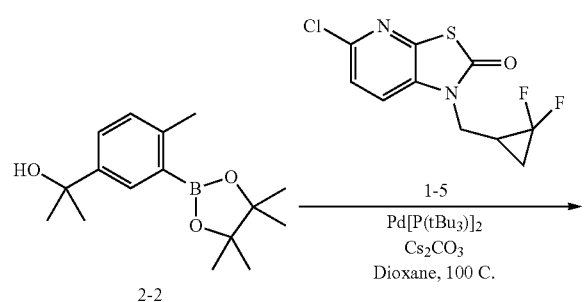

1-{[2,2-difluorocyclopropyl]methyl}-5-[5-(1-hydroxy-1-methylethyl)-2-methylphenyl][1,3]thiazolo[5,4-b]pyridin-2(1H)-one (2-3)

2-(3-bromo-4-methylphenyl)propan-2-ol (2-1)

To a solution of methyl 3-bromo-4-methylbenzoate (25 g, 110 mmol) in THF (110 mL) at −78° C. under nitrogen was added methylmagnesium bromide (85 mL, 250 mmol, 3M in THF) slowly and allowed to stir for 30 minutes. The reaction was warmed to room temperature for 30 minutes and the solution was diluted with ethyl acetate and sodium bicarbonate. The solution was then extracted with ethyl acetate, washed the combined organic layers with brine, dried over sodium sulfate, filtered and concentrated to afford 2-(3-bromo-4-methylphenyl)propan-2-ol (2-1) as a white solid.

2-[4-methyl-3-(4,4,5,5-tetramethyl-1,3,2-dioxaborolan-2-yl)phenyl]propan-2-ol (2-2)

A mixture of 2-(3-bromo-4 methylphenyl)propan-2-ol (2-1) (10 g, 44 mmol), bispinacoloto(diboron) (12 g, 48 mmol), potassium acetate (13 g, 130 mmol) and Pd(dppf)Cl₂

(2.1 g, 2.9 mmol) was heated in dioxane (44 mL) under nitrogen at 90° C. overnight. The suspension was cooled to room temperature, diluted with ethyl acetate and filtered. The resulting filtrate was washed with sodium bicarbonate, brine, dried over sodium sulfate, filtered and concentrated. The compound was purified using silica gel chromatography (0-80% ethyl acetate/hexanes) to give 2-[4-methyl-3-(4,4,5,5-tetramethyl-1,3,2-dioxaborolan-2-yl)phenyl]propan-2-ol (2-2) as a white solid.

1-{[2,2-difluorocyclopropyl]methyl}-5-[5-(1-hydroxy-1-methylethyl)-2-methylphenyl][1,3]thiazolo[5,4-b]pyridin-2(1H)-one (2-3)

Prepared from 1-5 according to the procedures reported in Scheme 1. $^1$H NMR (400 MHz, CD$_3$OD): δ 7.72 (d, J=8.4 Hz, 1H); 7.46 (d, J=8.3 Hz, 2H); 7.40 (dd, J=8.0, 2.1 Hz, 1H); 7.23 (d, J=8.0 Hz, 1H); 4.29-4.07 (m, 2H); 2.29 (s, 3H); 2.25-2.15 (m, 1H); 1.65-1.53 (m, 1H); 1.52 (s, 6H); 1.47-1.36 (m, 1H). HRMS (M+H)$^+$: observed=391.1283, calculated=391.1286.

SCHEME 3

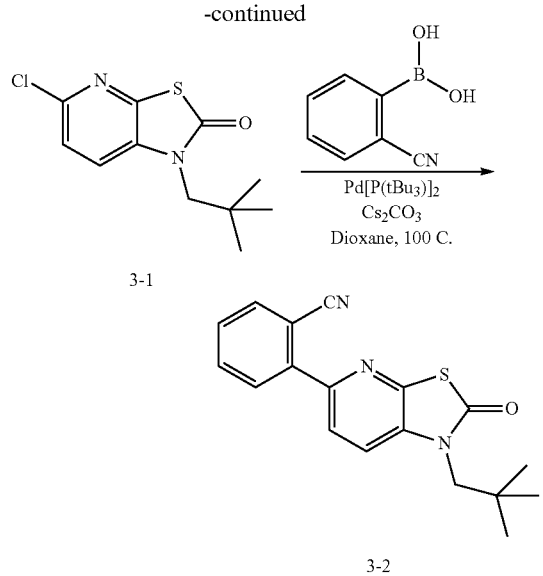

2-[1-(2,2-dimethylpropyl)-2-oxo-1,2-dihydro[1,3]thiazolo[5,4-b]pyridin-5-yl]benzonitrile (3-2)

Prepared from 1-4 according to the procedures reported in Scheme 1. $^1$H NMR (400 MHz, CD$_3$OD): δ 7.90-7.88 (m, 1H); 7.88-7.86 (m, 1H); 7.81 (s, 2H); 7.80-7.75 (m, 1H); 7.61-7.56 (m, 1H); 3.90 (s, 2H); 1.06 (s, 9H). HRMS (M+H)$^+$: observed=324.1162, calculated=324.1165.

TABLE 2

The following compounds were prepared from 3-1 by a reaction sequence analogous to that illustrated in Scheme 3.

| Cmpd | Structure | IUPAC Name | Exact Mass [M + H]+ |
| --- | --- | --- | --- |
| 3-3 | 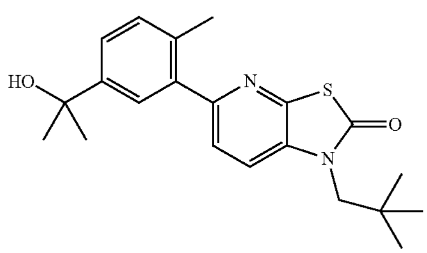 [SMILES: Cc1ccc(C(C)(C)O)cc1-c1ccc2c(n1)sc(=O)n2CC(C)(C)C] | 1-(2,2-dimethylpropyl)-5-[5-(1-hydroxy-1-methylethyl)-2-methyphenyl][1,3]thiazolo[5,4-b]pyridin-2(1H)-one | Calc'd 371.1788, found 371.1781 |
| 3-4 | 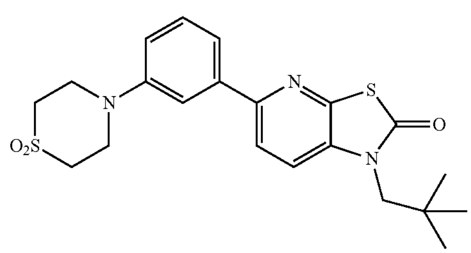 [SMILES: CC(C)(C)Cn1c(=O)sc2nc(-c3cccc(N4CCS(=O)(=O)CC4)c3)ccc21] | 1-(2,2-dimethypropyl)-5-[3-(1,1-dioxidothiomorpholin-4-yl)phenyl][1,3]thiazolo[5,4-b]pyridin-2(1H)-one | Calc'd 432.141, found 432.141 |

SCHEME 4

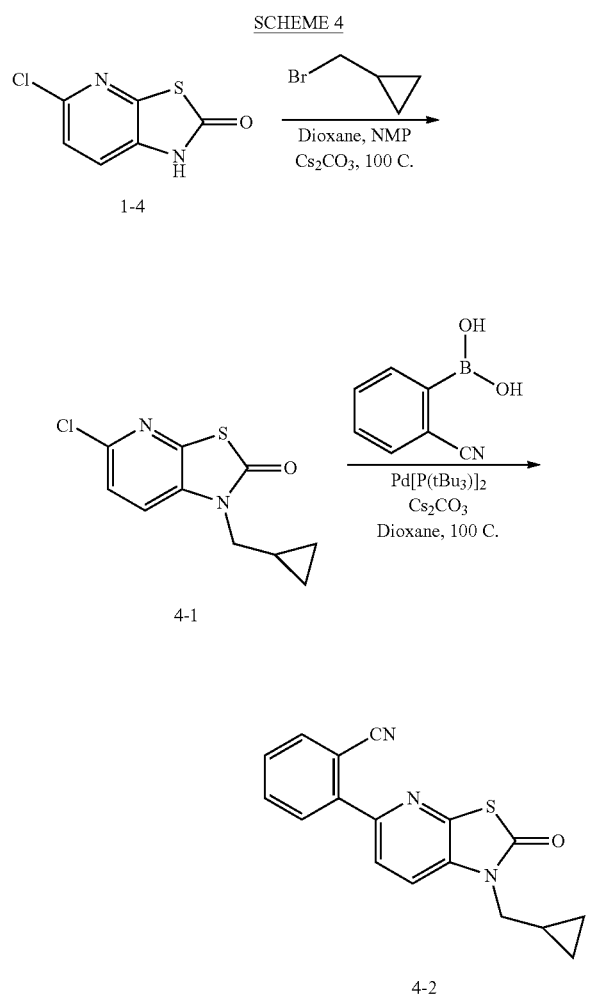

2-[1-(cyclopropylmethyl)-2-oxo-1,2-dihydro[1,3]thiazolo[5,4-b]pyridin-5-yl]benzonitrile (4-2)

Prepared from 1-4 according to the procedures reported in Scheme 1. HRMS (M+H)+: observed=308.0849, calculated=308.0852.

SCHEME 5

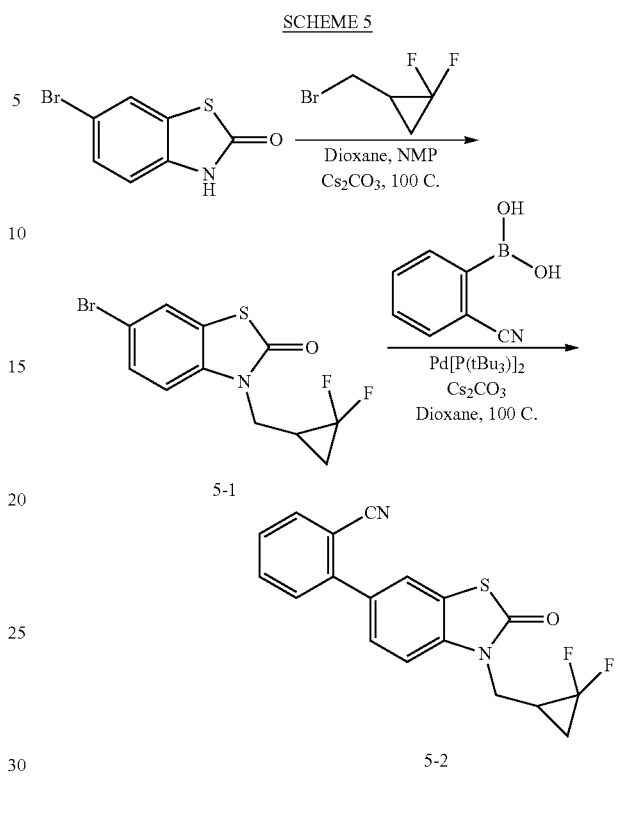

2-(3-{[2,2-difluorocyclopropyl]methyl}-2-oxo-2,3-dihydro-1,3-benzothiazol-6-yl)benzonitrile (5-2)

6-bromo-3-[(2,2-difluorocyclopropyl)methyl]-1,3-benzothiazol-2(3H)-one (5-1)

To a round bottom flask was added 6-bromo-1,3-benzothiazol-2(3H)-one (11.1 g, 48.5 mmol), anhydrous NMP (10 mL), anhydrous 1,4-dioxane (100 mL), cesium carbonate (33.2 g, 102 mmol), followed by 2-(bromomethyl)-1,1-difluorocyclopropane (8.29 g, 48.5 mmol). The reaction mixture was then heated to 95° C. while stirring in a hot oil bath with a water cooled reflux condenser attached under an atmosphere of nitrogen for 18 hours. The crude reaction mixture was then cooled to room temperature, suspended in ethyl

TABLE 3

The following compound was prepared from 4-1 by a reaction sequence analogous to that illustrated in Scheme 4.

| Cmpd | Structure | IUPAC Name | Exact Mass [M + H]+ |
|---|---|---|---|
| 4-3 | | 1-(cyclopropylmethyl)-5-[3-(1,1-dioxidothiomorpholin-4-yl)phenyl][1,3]thiazolo[5,4-b]pyridin-2(1H)-one | Calc'd 416.1097, found 416.1096 | acetate and washed with a saturated solution of sodium bicarbonate, followed by water, then brine, dried over sodium sulfate, filtered, and concentrated. The resulting residue was then purified by silica gel chromatography (0-30% EtOAc/Hex) to give 6-bromo-3-[(2,2-difluorocyclopropyl)methyl]-1,3-benzothiazol-2(3H)-one (1-1) as a white solid. HRMS (M+H)+: observed=319.9550, calculated=319.9551.

2-(3-{[2,2-difluorocyclopropyl]methyl}-2-oxo-2,3-dihydro-1,3-benzothiazol-6-yl)benzonitrile (5-2)

Prepared from 5-1 according to the procedures reported in Scheme 1. $^1$H NMR (400 MHz, CD$_3$OD): δ 7.84 (d, J=7.8 Hz, 1H); 7.81-7.69 (m, 2H); 7.64-7.57 (m, 2H); 7.54 (t, J=7.7 Hz, 1H); 7.48 (d, J=8.4 Hz, 1H); 4.30-4.12 (m, 2H); 2.27-2.16 (m, 1H); 1.66-1.54 (m, 1H); 1.48-1.38 (m, 1H). HRMS (M+H)+: observed=343.0705, calculated=343.0711.

TABLE 4

The following compound was prepared from 5-1 by a reaction sequence analogous to that illustrated in Scheme 1.

| Cmpd | Structure | IUPAC Name | Exact Mass [M + H]+ |
|---|---|---|---|
| 5-3 | 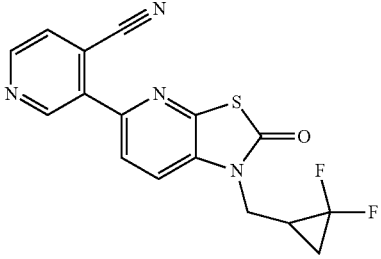 [SMILES: N#Cc1ccncc1-c1ccc2c(n1)sc(=O)n2CC1CC1(F)F] | 3-(3-{[2,2-difluorocyclopropyl]methyl}-2-oxo-2,3-dihydro-1,3-benzothiazol-6-yl)pyridine-4-carbonitrile | Calc'd 344.0664, found 344.0664 |
| 5-4 | 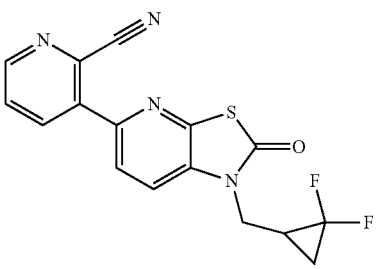 [SMILES: N#Cc1ncccc1-c1ccc2c(n1)sc(=O)n2CC1CC1(F)F] | 3-(3-{[2,2-difluorocyclopropyl]methyl}-2-oxo-2,3-dihydro-1,3-benzothiazol-6-yl)pyridine-2-carbonitrile | Calc'd 344.0664, found 344.0657 |
| 5-5 | 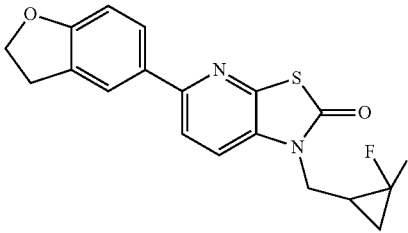 | 3-{[2,2-difluorocyclopropyl]methyl}-6-(2,3-dihydro-1-benzofuran-5-yl)-1,3-benzothiazol-2(3H)-one | Calc'd 360.0864, found 360.0855 |
| 5-6 | 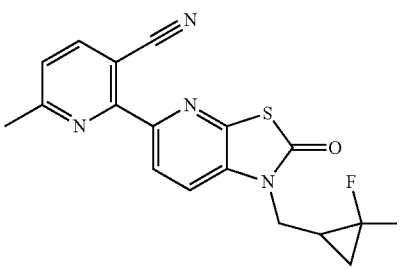 | 2-(3-{[2,2-difluorocyclopropyl]methyl}-2-oxo-2,3-dihydro-1,3-benzothiazol-6-yl)-6-methylpyridine-3-carbonitrile | Calc'd 358.0820, found 358.0812 |

TABLE 4-continued

The following compound was prepared from 5-1 by a reaction sequence analogous to that illustrated in Scheme 1.

| Cmpd | Structure | IUPAC Name | Exact Mass [M + H]+ |
|---|---|---|---|
| 5-7 | 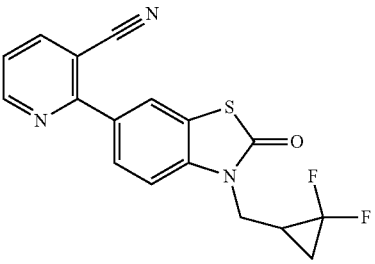 [SMILES: N#Cc1cccnc1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)pyridine-3-carbonitrile | Calc'd 344.0664, found 344.0657 |
| 5-8 | 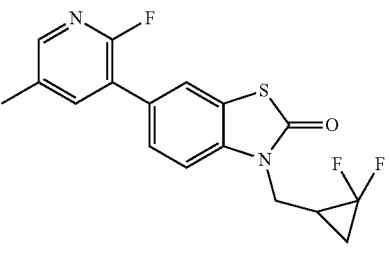 [SMILES: Cc1cnc(F)c(-c2ccc3c(c2)sc(=O)n3CC2CC2(F)F)c1] | 3-{[2,2-difluorocyclopropyl]methyl}-6-(2-fluoro-5-methylpyridin-3-yl)-1,3-benzothiazol-2(3H)-one | Calc'd 351.0773 found 351.0766 |
| 5-9 | 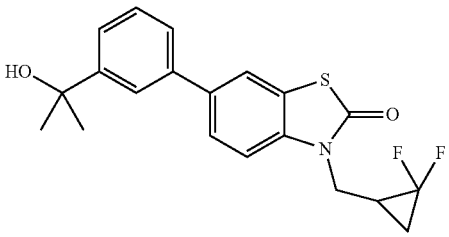 | 3-{[2,2-difluorocyclopropyl]methyl}-6-[3-(1-hydroxy-1-methylethyl)phenyl]-1,3-benzothiazol-2(3H)-one | Calc'd 376.1177, found 376.1169 |
| 5-10 | 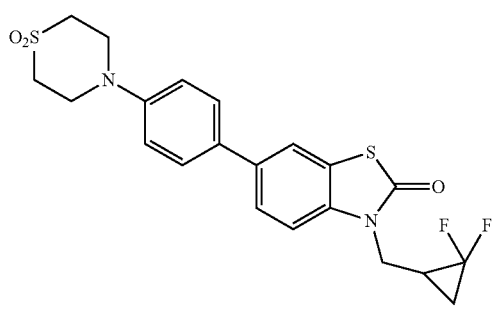 [SMILES: O=c1sc2cc(-c3ccc(N4CCS(=O)(=O)CC4)cc3)ccc2n1CC1CC1(F)F] | 3-{[2,2-difluorocyclopropyl]methyl}-6-[4-(1,1-dioxidothiomorpholin-4-yl)phenyl]-1,3-benzothiazol-2(3H)-one | Calc'd 451.0956, found 451.0942 |
| 5-11 | 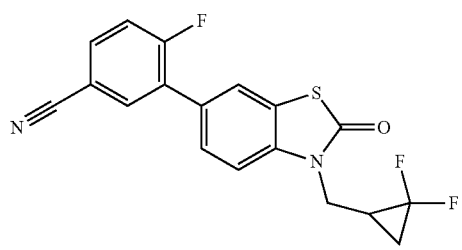 [SMILES: N#Cc1ccc(F)c(-c2ccc3c(c2)sc(=O)n3CC2CC2(F)F)c1] | 3-(3-{[2,2-difluorocyclopropyl]methyl}-2-oxo-2,3-dihydro-1,3-benzothiazol-6-yl)-4-fluorobenzonitrile | Calc'd 361.0617, found 361.0611 |

TABLE 4-continued

The following compound was prepared from 5-1 by a reaction sequence analogous to that illustrated in Scheme 1.

| Cmpd | Structure | IUPAC Name | Exact Mass [M + H]+ |
|---|---|---|---|
| 5-12 | 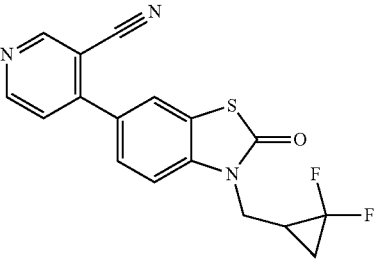 [SMILES: N#Cc1cnccc1-c1ccc2c(c1)sc(=O)n2CC1CC1(F)F] | 4-(3-{[2,2-difluorocyclopropyl]methyl}-2-oxo-2,3-dihydro-1,3-benzothiazol-6-yl)pyridine-3-carbonitrile | Calc'd 344.0664 344.0657 |
| 5-13 | 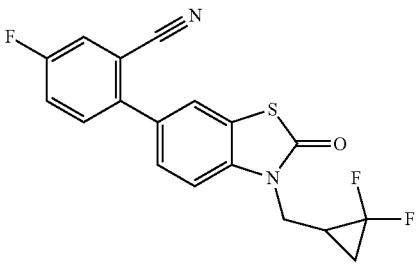 [SMILES: N#Cc1cc(F)ccc1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-5-fluorobenzonitrile | Calc'd 361.0617, found 361.0611 |
| 5-14 | 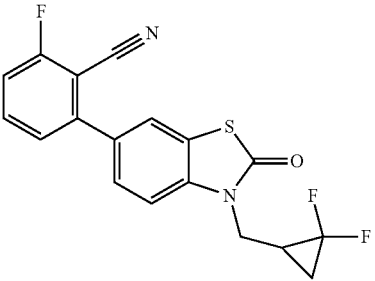 [SMILES: N#Cc1c(F)cccc1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-6-fluorobenzonitrile | Calc'd 361.0617, found 361.0609 |
| 5-15 | 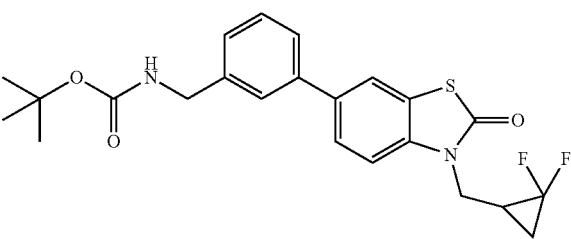 [SMILES: CC(C)(C)OC(=O)NCc1cccc(-c2ccc3c(c2)sc(=O)n3CC2CC2(F)F)c1] | tert-butyl [3-(3-{[2,2-difluorocyclopropyl]methyl}-2-oxo-2,3-dihydro-1,3-benzothiazol-6-yl)benzyl]carbamate | Calc'd 447.1548, found 447.1535 |
| 5-16 | 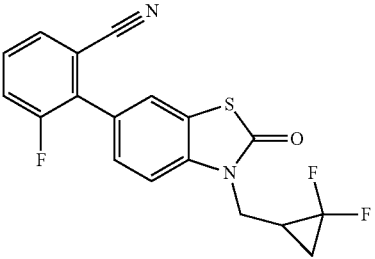 [SMILES: N#Cc1cccc(F)c1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-3-fluorobenzonitrile | Calc'd 361.0617, found 361.061 |

TABLE 4-continued

The following compound was prepared from 5-1 by a reaction sequence analogous to that illustrated in Scheme 1.

| Cmpd | Structure | IUPAC Name | Exact Mass [M + H]+ |
| --- | --- | --- | --- |
| 5-17 | 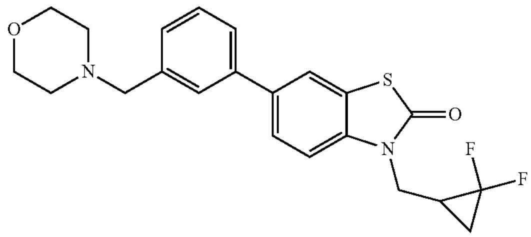 [SMILES: O=c1sc2cc(-c3cccc(CN4CCOCC4)c3)ccc2n1CC1CC1(F)F] | 3-{[2,2-difluorocyclopropyl]methyl}-6-[3-(morpholin-4-ylmethyl)phenyl]-1,3-benzothiazol-2(3H)-one | Calcd 417.1443, found 417.1432 |
| 5-18 | 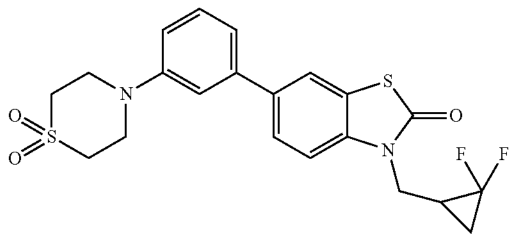 [SMILES: O=c1sc2cc(-c3cccc(N4CCS(=O)(=O)CC4)c3)ccc2n1CC1CC1(F)F] | 3-{[2,2-difluorocyclopropyl]methyl}-6-[3-(1,1-dioxidothiomorpholin-4-yl)phenyl]-1,3-benzothiazol-2(3H)-one | Calc'd 451.0956, found 451.0941 |
| 5-19 | 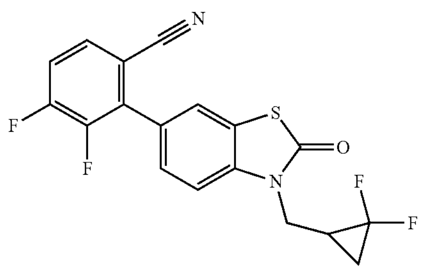 [SMILES: N#Cc1ccc(F)c(F)c1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-3,4-difluorobenzonitrile | Calc'd 379.0523, found 379.0528 |
| 5-20 | 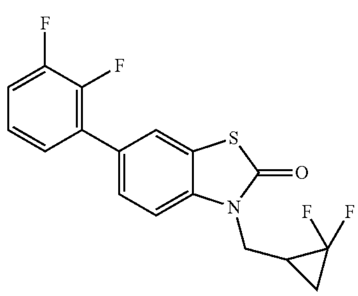 [SMILES: O=c1sc2cc(-c3cccc(F)c3F)ccc2n1CC1CC1(F)F] | 3-{[2,2-difluorocyclopropyl]methyl}-6-(2,3-difluorophenyl)-1,3-benzothiazol-2(3H)-one | Calc'd 354.057, found 354.0568 |
| 5-21 | 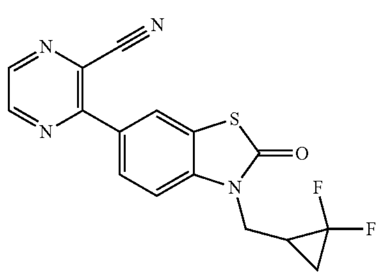 [SMILES: N#Cc1nccnc1-c1ccc2c(c1)sc(=O)n2CC1CC1(F)F] | 3-(3-{[2,2-difluorocyclopropyl]methyl}-2-oxo-2,3-dihydro-1,3-benzothiazol-6-yl)pyrazine-2-carbonitrile | Calc'd 345.0616, found 345.0619 |

TABLE 4-continued

The following compound was prepared from 5-1 by a reaction sequence analogous to that illustrated in Scheme 1.

| Cmpd | Structure | IUPAC Name | Exact Mass [M + H]+ |
| --- | --- | --- | --- |
| 5-22 | 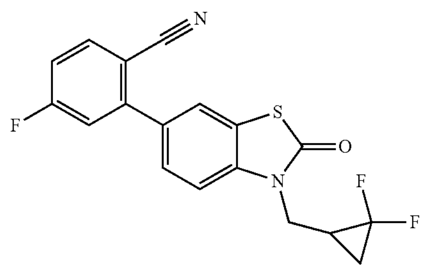 [SMILES: N#Cc1ccc(F)cc1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-4-fluorobenzonitrile | Calc'd 361.0617, found 361.0618 |
| 5-23 | 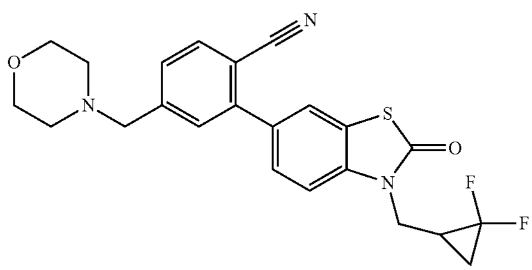 [SMILES: N#Cc1ccc(CN2CCOCC2)cc1-c1ccc2c(c1)sc(=O)n2CC1CC1(F)F] | 2-(3-{[2,2-difluoropropyl]methyl}-2-oxo-2,3-dihydro-1,3-benzothiazol-6-yl)-4-(morpholin-4-ylmethyl)benzonitrile | Calc'd 442.1395, found 442.1399 |
| 5-24 | 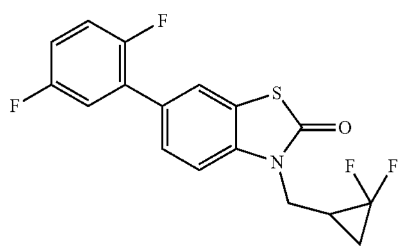 [SMILES: O=c1sc2cc(-c3cc(F)ccc3F)ccc2n1CC1CC1(F)F] | 3-{[2,2-difluorocyclopropyl]methyl}-6-(2,5-difluorophenyl)-1,3-benzothiazol-2(3H)-one | Calc'd 354.0570, found 354.0571 |
| 5-25 | 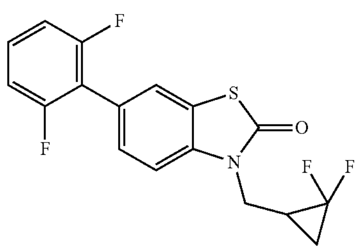 [SMILES: O=c1sc2cc(-c3c(F)cccc3F)ccc2n1CC1CC1(F)F] | 3-{[2,2-difluorocyclopropyl]methyl}-6-(2,6-difluorophenyl)-1,3-benzothiazol-2(3H)-one | Calc'd 354.0570, found 354.0571 |
| 5-26 | 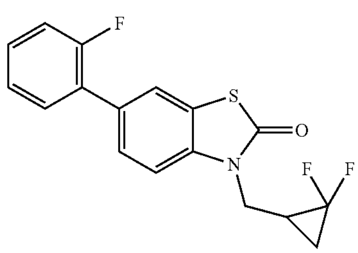 [SMILES: O=c1sc2cc(-c3ccccc3F)ccc2n1CC1CC1(F)F] | 3-{[2,2-difluorocyclopropyl]methyl}-6-(2-fluorophenyl)-1,3-benzothiazol-2(3H)-one | Calc'd 336.0664, found 336.0664 |

TABLE 4-continued

The following compound was prepared from 5-1 by a reaction sequence analogous to that illustrated in Scheme 1.

| Cmpd | Structure | IUPAC Name | Exact Mass [M + H]+ |
|---|---|---|---|
| 5-27 | 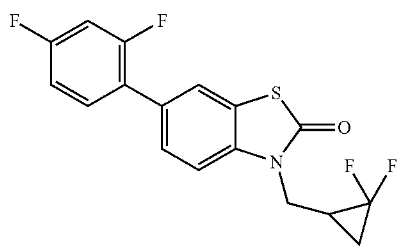 [SMILES: O=c1sc2cc(-c3ccc(F)cc3F)ccc2n1CC1CC1(F)F] | 3-{[2,2-difluorocyclopropyl]methyl}-6-(2,4-difluorophenyl)-1,3-benzothiazol-2(3H)-one | Calc'd 354.057 354.057 |
| 5-28 | 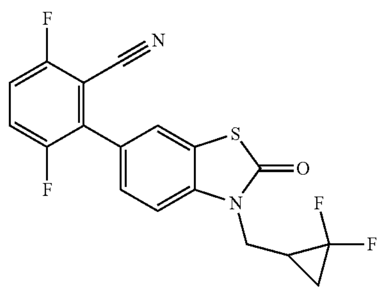 [SMILES: N#Cc1c(F)ccc(F)c1-c1ccc2c(c1)sc(=O)n2CC1CC1(F)F] | 2-(3-{[2,2-difluorocyclopropyl]methyl}-2-oxo-2,3-dihydro-1,3-benzothiazol-6-yl)-3,6-difluorobenzonitrile | Calc'd 379.0523, found 379.0524 |
| 5-29 | 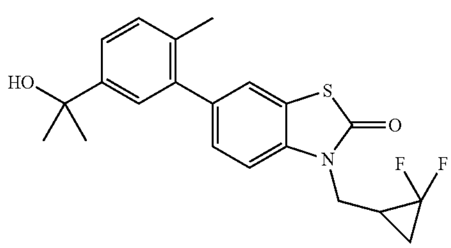 [SMILES: Cc1ccc(C(C)(C)O)cc1-c1ccc2c(c1)sc(=O)n2CC1CC1(F)F] | 3-{[2,2-difluorocyclopropyl]methyl}-6-[5-(1-hydroxy-1-methylethyl)-2-methylphenyl]-1,3-benzothiazol-2(3H)-one | Calc'd 390.1334, found 390.1342 |

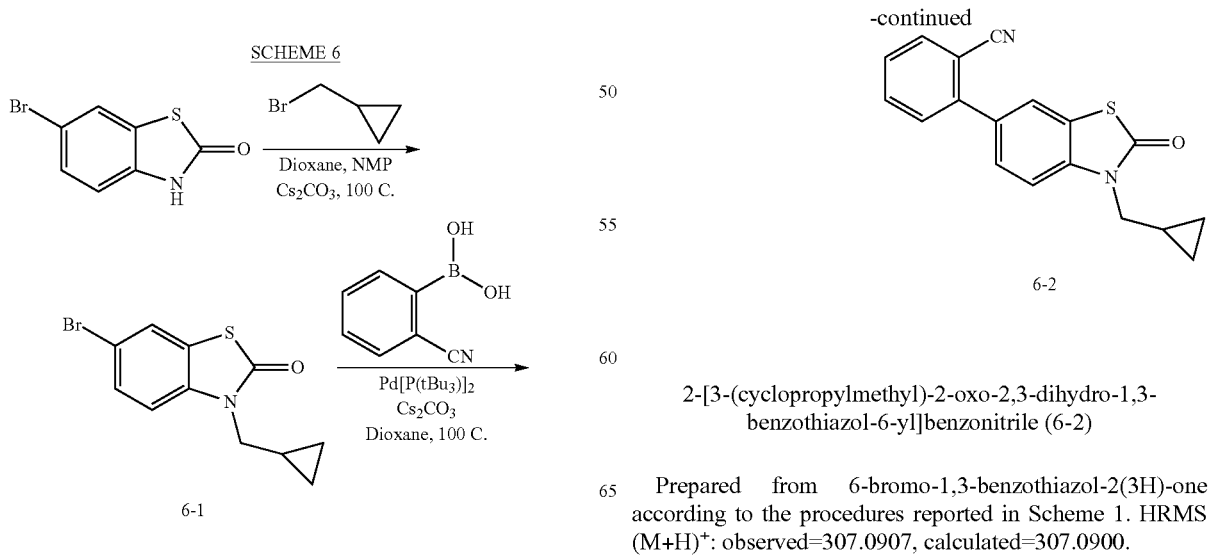

2-[3-(cyclopropylmethyl)-2-oxo-2,3-dihydro-1,3-benzothiazol-6-yl]benzonitrile (6-2)

Prepared from 6-bromo-1,3-benzothiazol-2(3H)-one according to the procedures reported in Scheme 1. HRMS (M+H)$^+$: observed=307.0907, calculated=307.0900.

TABLE 5

The following compound was prepared from 6-1 by a reaction sequence analogous to that illustrated in Scheme 1.

| Cmpd | Structure | IUPAC Name | Exact Mass [M + H]+ |
|---|---|---|---|
| 6-3 | 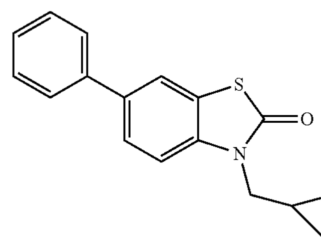 | 3-(cyclopropylmethyl)-6-phenyl-1,3-benzothiazol-2(3H)-one | Calc'd 282.0947, found 282.0953 |
| 6-4 | 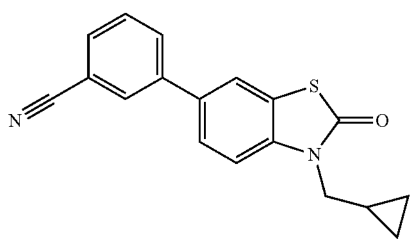 [SMILES: N#Cc1cccc(-c2ccc3c(c2)sc(=O)n3CC2CC2)c1] | 3-[3-(cyclopropylmethyl)-2-oxo-2,3-dihydro-1,3-benzothiazol-6-yl]benzonitrile | Calc'd 307.0900, found 307.0906 |
| 6-5 | 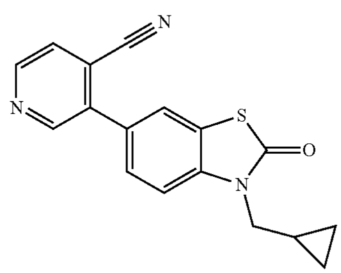 [SMILES: N#Cc1ccncc1-c1ccc2c(c1)sc(=O)n2CC1CC1] | 3-[3-(cyclopropylmethyl)-2-oxo-2,3-dihydro-1,3-benzothiazol-6-yl]pyridine-4-carbonitrile | Calc'd 308.0852, found 308.0849 |
| 6-6 | 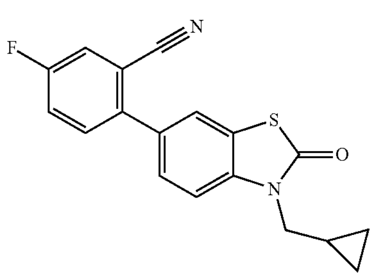 [SMILES: N#Cc1cc(F)ccc1-c1ccc2c(c1)sc(=O)n2CC1CC1] | 2-[3-(cyclopropylmethyl)-2-oxo-2,3-dihydro-1,3-benzothiazol-6-yl]-5-fluorobenzonitrile | Calc'd 325.0805, found 325.0804 |
| 6-7 | 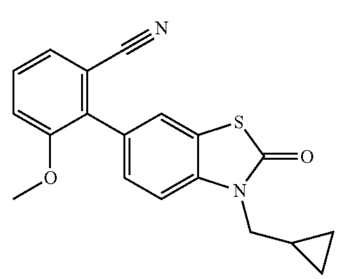 [SMILES: COc1cccc(C#N)c1-c1ccc2c(c1)sc(=O)n2CC1CC1] | 2-[3-(cyclopropylmethyl)-2-oxo-2,3-dihydro-1,3-benzothiazol-6-yl]-3-methoxybenzonitrile | Calc'd 337.1005, found 337.1007 |

TABLE 5-continued

The following compound was prepared from 6-1 by a reaction sequence analogous to that illustrated in Scheme 1.

| Cmpd | Structure | IUPAC Name | Exact Mass [M + H]+ |
|---|---|---|---|
| 6-8 | 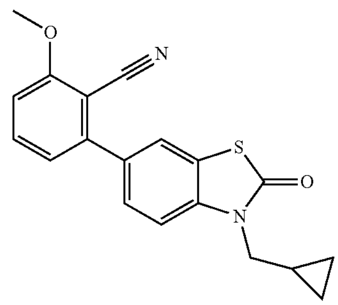 [SMILES: COc1cccc(-c2ccc3c(c2)sc(=O)n3CC2CC2)c1C#N] | 2-[3-(cyclopropylmethyl)-2-oxo-2,3-dihydro-1,3-benzothiazol-6-yl]-6-methoxybenzonitrile | Calc'd 337.1005, found 337.1005 |
| 6-9 | 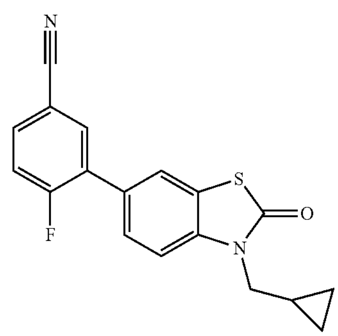 [SMILES: N#Cc1ccc(F)c(-c2ccc3c(c2)sc(=O)n3CC2CC2)c1] | 3-[3-(cyclopropylmethyl)-2-oxo-2,3-dihydro-1,3-benzothiazol-6-yl]-4-fluorobenzonitrile | Calc'd 325.0805, found 325.0803 |
| 6-10 | 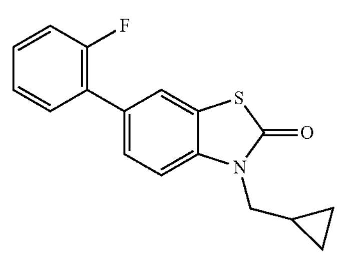 [SMILES: O=c1sc2cc(-c3ccccc3F)ccc2n1CC1CC1] | 3-(cyclopropylmethyl)-6-(2-fluorophenyl)-1,3-benzothiazol-2(3H)-one | Calc'd 300.0853, found 300.0847 |
| 6-11 | 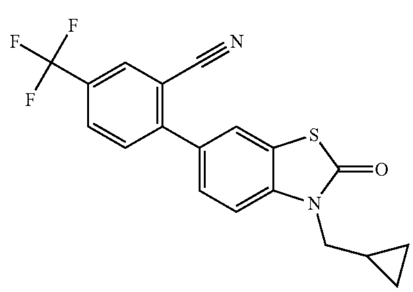 [SMILES: N#Cc1cc(C(F)(F)F)ccc1-c1ccc2c(c1)sc(=O)n2CC1CC1] | 2-[3-(cyclopropylmethyl)-2-oxo-2,3-dihydro-1,3-benzothiazol-6-yl]-5-(trifluoromethyl)benzonitrile | Calc'd 375.0773, found 375.0779 |

TABLE 5-continued

The following compound was prepared from 6-1 by a reaction sequence analogous to that illustrated in Scheme 1.

| Cmpd | Structure | IUPAC Name | Exact Mass [M + H]+ |
|---|---|---|---|
| 6-12 | 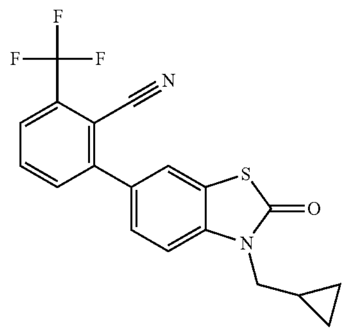 [SMILES: N#Cc1c(-c2ccc3c(c2)sc(=O)n3CC2CC2)cccc1C(F)(F)F] | 2-[3-(cyclopropylmethyl)-2-oxo-2,3-dihydro-1,3-benzothiazol-6-yl]-6-(trifluoromethyl)benzonitrile | Calc'd 375.0773, found 375.0779 |
| 6-13 | 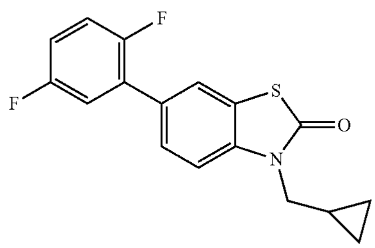 [SMILES: O=c1sc2cc(-c3cc(F)ccc3F)ccc2n1CC1CC1] | 3-(cyclopropylmethyl)-6-(2,5-difluorophenyl)-1,3-benzothiazol-2(3H)-one | Calc'd 318.0759, found 318.0757 |
| 6-14 | 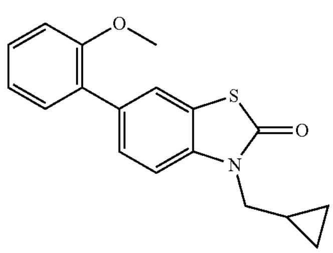 [SMILES: COc1ccccc1-c1ccc2c(c1)sc(=O)n2CC1CC1] | 3-(cyclopropylmethyl)-6-(2-methoxyphenyl)-1,3-benzothiazol-2(3H)-one | Calc'd 312.1053, found 312.1054 |
| 6-15 | 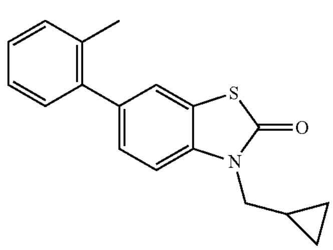 [SMILES: Cc1ccccc1-c1ccc2c(c1)sc(=O)n2CC1CC1] | 3-(cyclopropylmethyl)-6-(2-methylphenyl)-1,3-benzothiazol-2(3H)-one | Calc'd 296.1104, found 296.1103 |
| 6-16 | 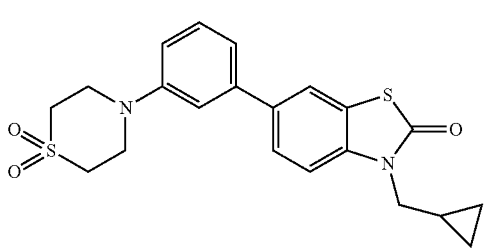 [SMILES: O=c1sc2cc(-c3cccc(N4CCS(=O)(=O)CC4)c3)ccc2n1CC1CC1] | 3-(cyclopropylmethyl)-6-[3-(1,1-dioxidothiomorpholin-4-yl)phenyl]-1,3-benzothiazol-2(3H)-one | Calc'd 415.1145, found 415.115 |

SCHEME 7

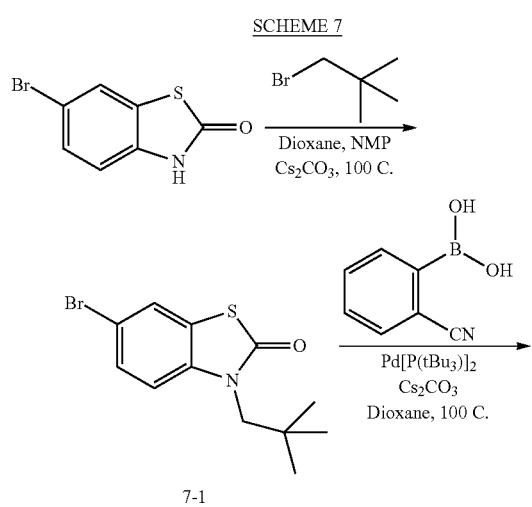

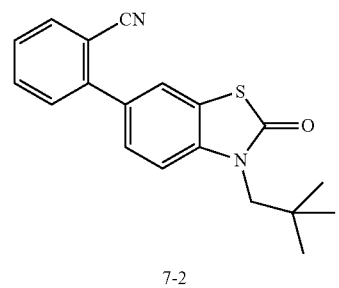

2-[3-(2,2-dimethylpropyl)-2-oxo-2,3-dihydro-1,3-benzothiazol-6-yl]benzonitrile (7-2)

Prepared from 6-bromo-1,3-benzothiazol-2(3H)-one according to the procedures reported in Scheme 1. HRMS $(M+H)^+$: observed=323.1219, calculated=323.1213.

TABLE 6

The following compound was prepared from 7-1 by a reaction sequence analogous to that illustrated in Scheme 7.

| Cmpd | Structure | IUPAC Name | Exact Mass [M + H]+ |
|---|---|---|---|
| 7-3 | 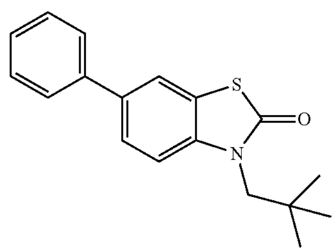 [SMILES: CC(C)(C)Cn1c(=O)sc2cc(-c3ccccc3)ccc21] | 3-(2,2-dimethylpropyl)-6-phenyl-1,3-benzothiazol-2(3H)-one | Calc'd 298.1260, found 298.1265 |
| 7-4 | 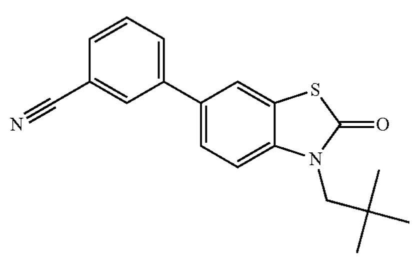 [SMILES: CC(C)(C)Cn1c(=O)sc2cc(-c3cccc(C#N)c3)ccc21] | 3-[3-(2,2-dimethylpropyl)-2-oxo-2,3-dihydro-1,3-benzothiazol-6-yl]benzonitrile | Calc'd 323.1213, found 323.1221 |
| 7-5 | 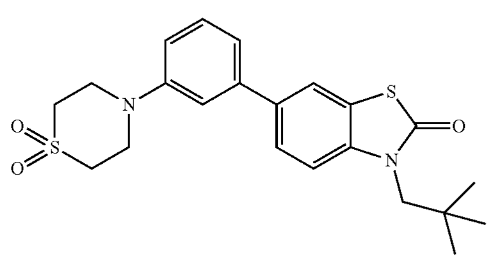 [SMILES: CC(C)(C)Cn1c(=O)sc2cc(-c3cccc(N4CCS(=O)(=O)CC4)c3)ccc21] | 3-(2,2-dimethylpropyl)-6-[3-(1,1-dioxidothiomorpholin-4-yl)phenyl]-1,3-benzothiazol-2(3H)-one | Calc'd 431.1458, found 431.1465 |

SCHEME 8

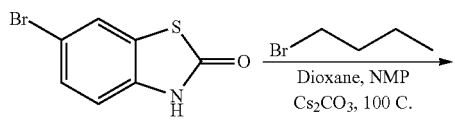

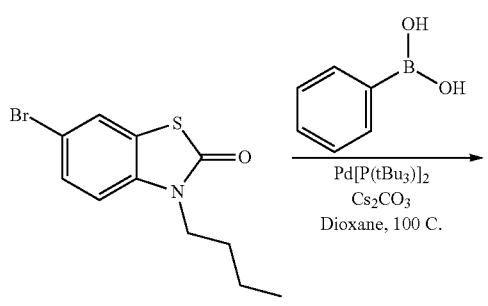

8-1

SCHEME 9

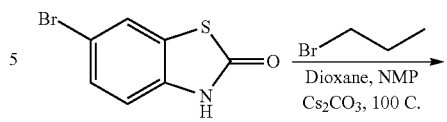

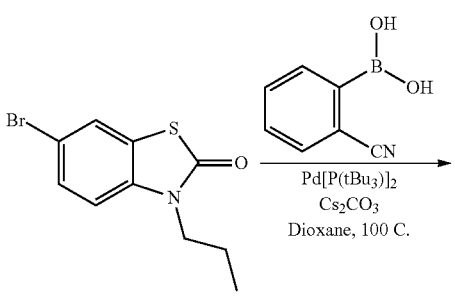

9-1

3-butyl-6-phenyl-1,3-benzothiazol-2(3H)-one (8-2)

Prepared from 6-bromo-1,3-benzothiazol-2(3H)-one according to the procedures reported in Scheme 1. HRMS (M+H)$^+$: observed=284.1108, calculated=284.1104.

2-(2-oxo-3-propyl-2,3-dihydro-1,3-benzothiazol-6-yl)benzonitrile (9-2)

Prepared from 6-bromo-1,3-benzothiazol-2(3H)-one according to the procedures reported in Scheme 1. HRMS (M+H)$^+$: observed=295.0899, calculated=295.0900.

TABLE 7

The following compound was prepared from 6-bromo-1,3-benzothiazol-2(3H)-one by a reaction sequence analogous to that illustrated in Scheme 8.

| Cmpd | Structure | IUPAC Name | Exact Mass [M + H]+ |
|---|---|---|---|
| 8-3 | 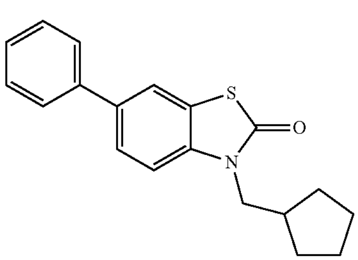 [SMILES: O=c1sc2cc(-c3ccccc3)ccc2n1CC1CCCC1] | 3-(cyclopentylmethyl)-6-phenyl-1,3-benzothiazol-2(3H)-one | Calc'd 310.1260, found 310.1268 |

TABLE 8

The following compounds were prepared from 6-bromo-1,3-benzothiazol-2(3H)-one by a reaction sequence analogous to that illustrated in Scheme 9.

| Cmpd | Structure | IUPAC Name | Exact Mass [M + H]+ |
|---|---|---|---|
| 9-3 | 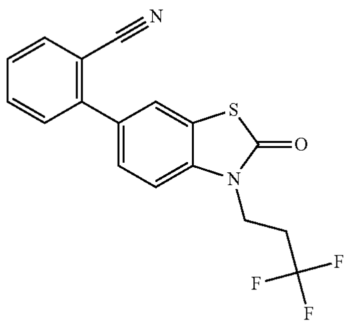 [SMILES: N#Cc1ccccc1-c1ccc2c(c1)sc(=O)n2CCC(F)(F)F] | 2-[2-oxo-3-(3,3,3-trifluoropropyl)-2,3-dihydro-1,3-benzothiazol-6-yl]benzonitrile | Calc'd 349.0617, found 349.0617 |
| 9-4 | 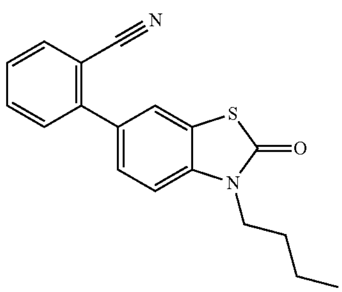 [SMILES: CCCCn1c(=O)sc2cc(-c3ccccc3C#N)ccc21] | 2-(3-butyl-2-oxo-2,3-dihydro-1,3-benzothiazol-6-yl)benzonitrile | Calc'd 309.1056, found 309.1063 |
| 9-5 | 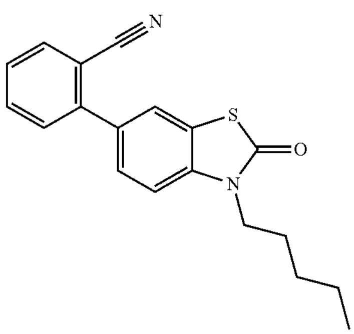 [SMILES: CCCCCn1c(=O)sc2cc(-c3ccccc3C#N)ccc21] | 2-(2-oxo-3-pentyl-2,3-dihydro-1,3-benzothiazol-6-yl)benzonitrile | Calc'd 323.1213, found 323.1220 |
| 9-6 | 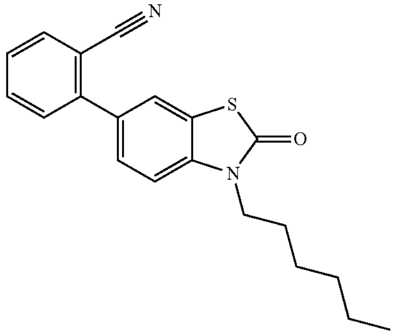 [SMILES: CCCCCCn1c(=O)sc2cc(-c3ccccc3C#N)ccc21] | 2-(3-hexyl-2-oxo-2,3-dihydro-1,3-benzothiazol-6-yl)benzonitrile | Calc'd 337.1369, found 337.1377 |

TABLE 8-continued

The following compounds were prepared from 6-bromo-1,3-benzothiazol-2(3H)-one by a
reaction sequence analogous to that illustrated in Scheme 9.

| Cmpd | Structure | IUPAC Name | Exact Mass [M + H]+ |
|---|---|---|---|
| 9-7 | 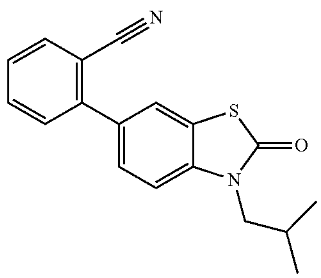 [SMILES: CC(C)Cn1c(=O)sc2cc(-c3ccccc3C#N)ccc21] | 2-[3-(2-methylpropyl)-2-oxo-2,3-dihydro-1,3-benzothiazol-6-yl]benzonitrile | Calc'd 309.1056, found 309.1057 |
| 9-8 | 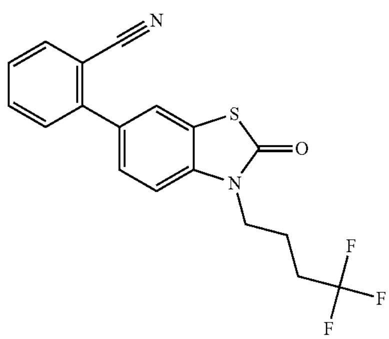 [SMILES: N#Cc1ccccc1-c1ccc2c(c1)sc(=O)n2CCCC(F)(F)F] | 2-[2-oxo-3-(4,4,4-trifluorobutyl)-2,3-dihydro-1,3-benzothiazol-6-yl]benzonitrile | Calc'd 363.0773, found 363.0775 |
| 9-9 | 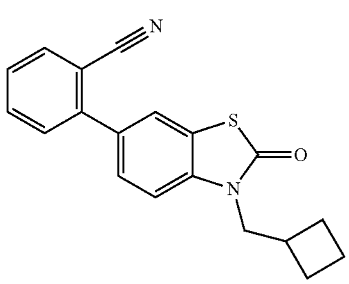 [SMILES: N#Cc1ccccc1-c1ccc2c(c1)sc(=O)n2CC1CCC1] | 2-[3-(cyclobutylmethyl)-2-oxo-2,3-dihydro-1,3-benzothiazol-6-yl]benzonitrile | Calc'd 321.1056, found 321.1064 |
| 9-10 | 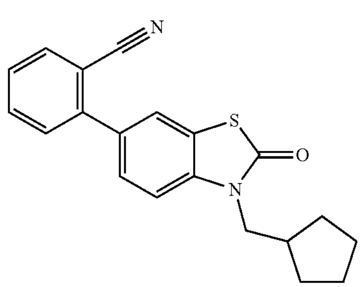 [SMILES: N#Cc1ccccc1-c1ccc2c(c1)sc(=O)n2CC1CCCC1] | 2-[3-(cyclopentylmethyl)-2-oxo-2,3-dihydro-1,3-benzothiazol-6-yl]benzonitrile | Calc'd 335.1213, found 335.1221 |

TABLE 8-continued

*The following compounds were prepared from 6-bromo-1,3-benzothiazol-2(3H)-one by a reaction sequence analogous to that illustrated in Scheme 9.*

| Cmpd | Structure | IUPAC Name | Exact Mass [M + H]+ |
|---|---|---|---|
| 9-11 | 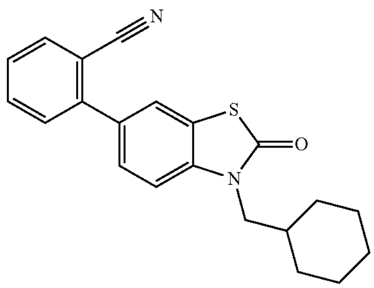 [SMILES: N#Cc1ccccc1-c1ccc2c(c1)sc(=O)n2CC1CCCCC1] | 2-[3-(cyclohexylmethyl)-2-oxo-2,3-dihydro-1,3-benzothiazol-6-yl]benzonitrile | Calc'd 349.1369, found 349.1373 |
| 9-12 | 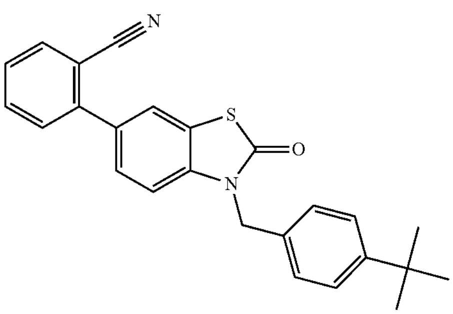 [SMILES: CC(C)(C)c1ccc(Cn2c(=O)sc3cc(-c4ccccc4C#N)ccc32)cc1] | 2-[3-(4-tert-butylbenzyl)-2-oxo-2,3-dihydro-1,3-benzothiazol-6-yl]benzonitrile | Calc'd 399.1526, found 399.1545 |
| 9-13 | 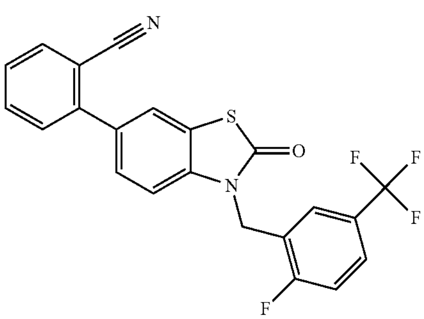 [SMILES: N#Cc1ccccc1-c1ccc2c(c1)sc(=O)n2Cc1cc(C(F)(F)F)ccc1F] | 2-{3-[2-fluoro-5-(trifluoromethyl)benzyl]-2-oxo-2,3-dihydro-1,3-benzothiazol-6-yl}benzonitrile | Calc'd 429.0679, found 429.069 |
| 9-14 | 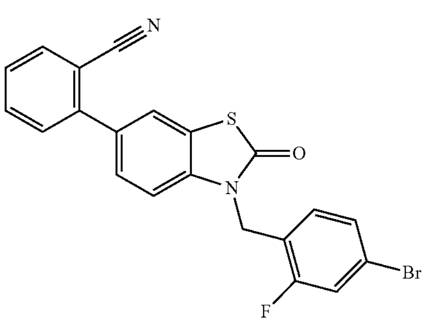 [SMILES: N#Cc1ccccc1-c1ccc2c(c1)sc(=O)n2Cc1ccc(Br)cc1F] | 2-[3-(4-bromo-2-fluorobenzyl)-2-oxo-2,3-dihydro-1,3-benzothiazol-6-yl]benzonitrile | Calc'd 438.9911, found 438.9912 |

TABLE 8-continued

The following compounds were prepared from 6-bromo-1,3-benzothiazol-2(3H)-one by a reaction sequence analogous to that illustrated in Scheme 9.

| Cmpd | Structure | IUPAC Name | Exact Mass [M + H]+ |
|---|---|---|---|
| 9-15 | 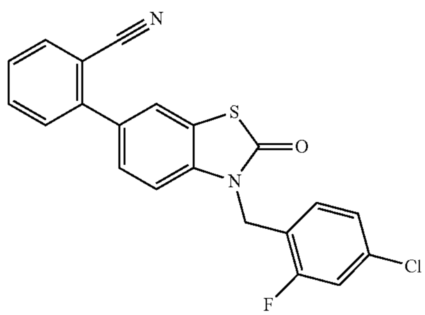 [SMILES: N#Cc1ccccc1-c1ccc2c(c1)sc(=O)n2Cc1ccc(Cl)cc1F] | 2-[3-(4-chloro-2-fluorobenzyl)-2-oxo-2,3-dihydro-1,3-benzothiazol-6-yl]benzonitrile | Calc'd 395.0416, found 395.0416 |
| 9-16 | 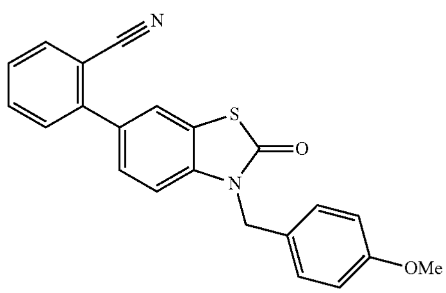 [SMILES: COc1ccc(Cn2c(=O)sc3cc(-c4ccccc4C#N)ccc32)cc1] | 2-[3-(4-methoxybenzyl)-2-oxo-2,3-dihydro-1,3-benzothiazol-6-yl]benzonitrile | Calc'd 373.1005, found 373.1006 |

SCHEME 10

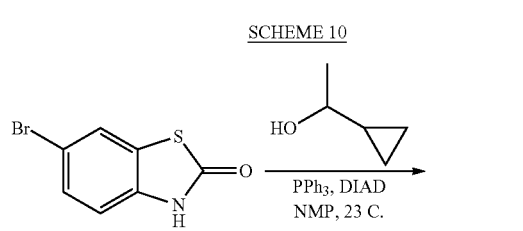

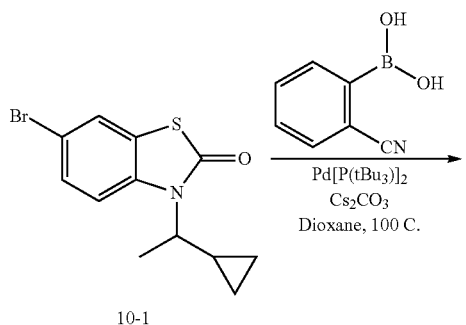

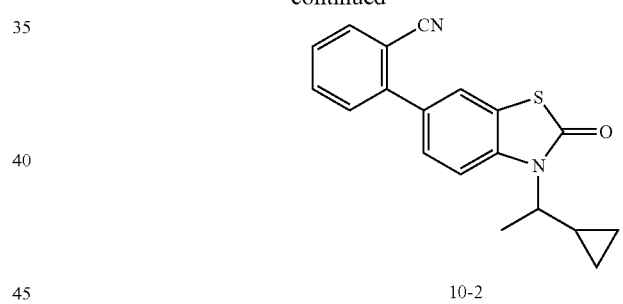

2-[3-(1-cyclopropylethyl)-2-oxo-2,3-dihydro-1,3-benzothiazol-6-yl]benzonitrile (10-2)

6-bromo-3-(1-cyclopropylethyl)-1,3-benzothiazol-2(3H)-one (10-1)

Prepared from 6-bromo-1,3-benzothiazol-2(3H)-one according to the procedures reported in Scheme 11. HRMS (M+H)⁺: observed=297.9894, calculated=297.9896.

2-[3-(1-cyclopropylethyl)-2-oxo-2,3-dihydro-1,3-benzothiazol-6-yl]benzonitrile (10-2)

Prepared from 6-bromo-1,3-benzothiazol-2(3H)-one according to the procedures reported in Scheme 1. HRMS (M+H)⁺: observed=321.1055, calculated=321.1056.

TABLE 9

The following compounds were prepared from 6-bromo-1,3-benzothiazol-2(3H)-one by a reaction sequence analogous to that illustrated in Scheme 10.

| Cmpd | Structure | IUPAC Name | Exact Mass [M + H]+ |
| --- | --- | --- | --- |
| 10-3 | 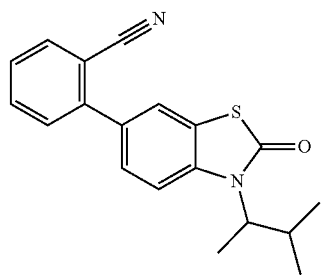 [SMILES: CC(C)C(C)n1c(=O)sc2cc(-c3ccccc3C#N)ccc21] | 2-{3-[1,2-dimethylpropyl]-2-oxo-2,3-dihydro-1,3-benzothiazol-6-yl}benzonitrile | Calc'd 323.1213, found 323.1214 |
| 10-4 | 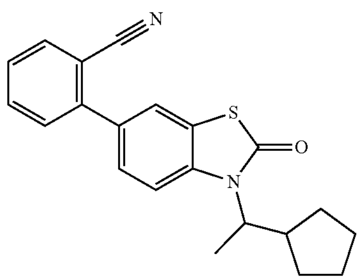 [SMILES: CC(C1CCCC1)n1c(=O)sc2cc(-c3ccccc3C#N)ccc21] | 2-{3-[1-cyclopentylethyl]-2-oxo-2,3-dihydro-1,3-benzothiazol-6-yl}benzonitrile | Calc'd 349.1369, found 349.1372 |
| 10-5 | 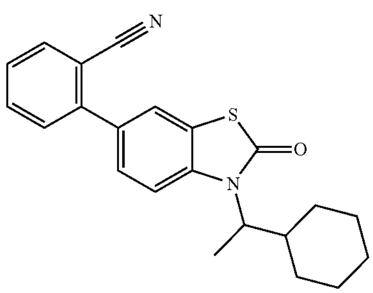 [SMILES: CC(C1CCCCC1)n1c(=O)sc2cc(-c3ccccc3C#N)ccc21] | 2-{3-[1-cyclohexylethyl]-2-oxo-2,3-dihydro-1,3-benzothiazol-6-yl}benzonitrile | Calc'd 363.1526, found 363.1525 |
| 10-6 | 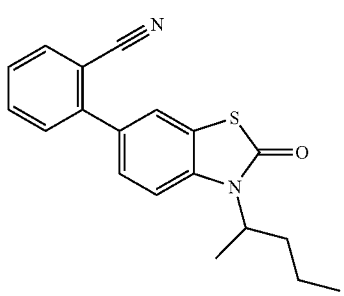 [SMILES: CCCC(C)n1c(=O)sc2cc(-c3ccccc3C#N)ccc21] | 2-{3-[1-methylbutyl]-2-oxo-2,3-dihydro-1,3-benzothiazol-6-yl}benzonitrile | Calc'd 323.1213, found 323.1206 |
| 10-7 | 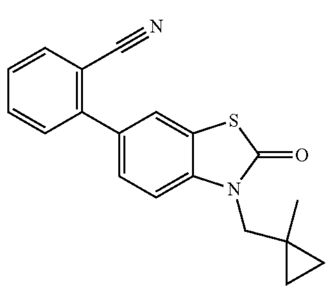 [SMILES: CC1(Cn2c(=O)sc3cc(-c4ccccc4C#N)ccc32)CC1] | 2-{3-[(1-methylcyclopropyl)methyl]-2-oxo-2,3-dihydro-1,3-benzothiazol-6-yl}benzonitrile | Calc'd 321.1056, found 321.1058 |

SCHEME 11

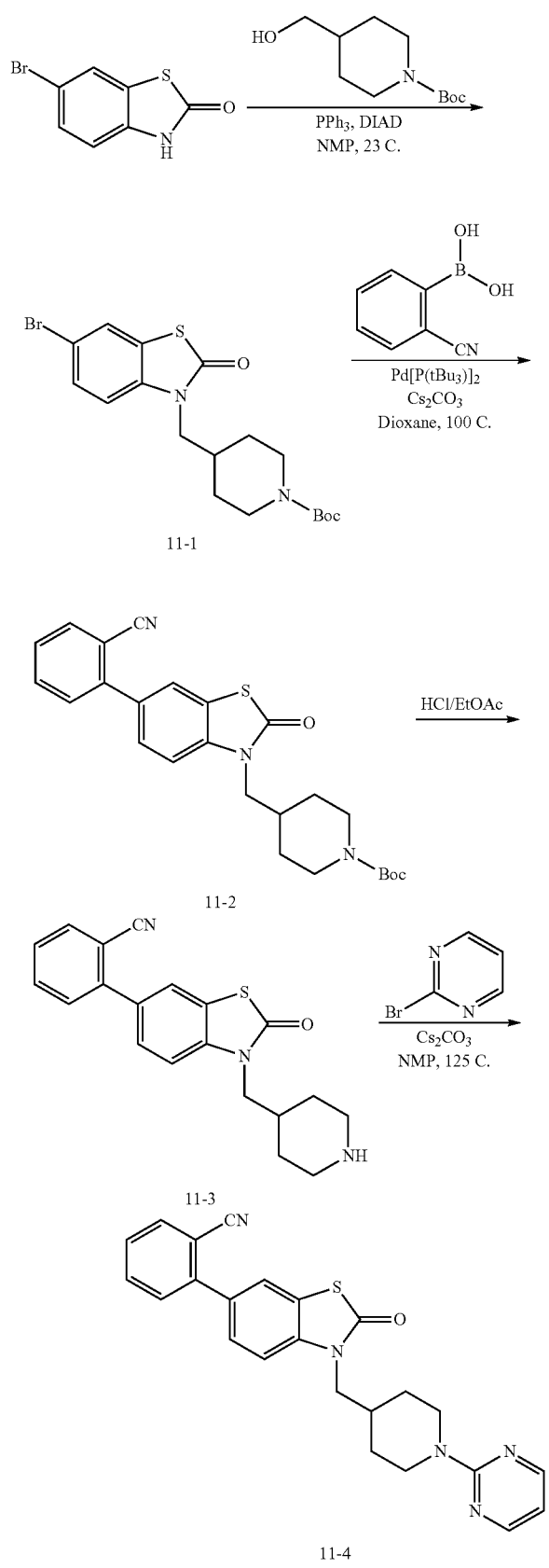

2-{2-oxo-3-[(1-pyrimidin-2-ylpiperidin-4-yl)methyl]-2,3-dihydro-1,3-benzothiazol-6-yl}benzonitrile (11-4)

tert-butyl 4-[(6-bromo-2-oxo-1,3-benzothiazol-3 (2H)-yl)methyl]piperidine-1-carboxylate (11-1)

To a round bottom flask was added 6-bromo-1,3-benzothiazol-2(3H)-one (0.300 g, 1.304 mmol), tert-butyl 4-(hydroxymethyl)piperidine-1-carboxylate (0.365 g, 1.695 mmol), triphenylphosphine (0.455 g, 1.695 mmol), diisopropyl (E)-diazene-1,2-dicarboxylate (DIAD) (0.330 mL, 1.695 mmol), and NMP (5 mL). The reaction mixture was then permitted to stir at room temperature for two hours. The crude reaction mixture was then diluted with methanol, filtered and concentrated. Purification of crude reaction mixture by reverse phase chromatography (Waters Sunfire MSC18, 30% acetonitrile/0.1% trifluoroacetic acid/water→100% acetonitrile/0.1% trifluoroacetic acid/water) tert-butyl 4-[(6-bromo-2-oxo-1,3-benzothiazol-3(2H)-yl)methyl]piperidine-1-carboxylate (11-1) as a tan solid. HRMS (M+H)$^+$: observed=427.0691, calculated=427.0686.

tert-butyl 4-{[6-(2-cyanophenyl)-2-oxo-1,3-benzothiazol-3(2H)-yl]methyl}piperidine-1-carboxylate (11-2)

Prepared from 11-1 according to the procedures reported in Scheme 1. HRMS (M+H)$^+$: observed=450.188, calculated=450.1773.

2-[2-oxo-3-(piperidin-4-ylmethyl)-2,3-dihydro-1,3-benzothiazol-6-yl]benzonitrile (11-3)

To a round bottom flask was added tert-butyl 4-{[6-(2-cyanophenyl)-2-oxo-1,3-benzothiazol-3(2H)-yl] methyl}piperidine-1-carboxylate (11-2) (0.242 g, 0.538 mmol), MeOH (2.5 mL), DCM (2.5 mL), and a sat'd solution of HCl in EtOAc (~4N) (1.346 mL, 5.38 mmol). The reaction mixture was capped and permitted to stir for two hours then concentrated to give 2-[2-oxo-3-(piperidin-4-ylmethyl)-2,3-dihydro-1,3-benzothiazol-6-yl]benzonitrile (11-3) as a tan solid. HRMS (M+H)$^+$: observed=350.1322, calculated=350.1322.

2-{2-oxo-3-[(1-pyrimidin-2-ylpiperidin-4-yl)methyl]-2,3-dihydro-1,3-benzothiazol-6-yl}benzonitrile (11-4)

To a microwave vial was added 2-[2-oxo-3-(piperidin-4-ylmethyl)-2,3-dihydro-1,3-benzothiazol-6-yl]benzonitrile (11-3) (0.029 g, 0.075 mmol), 2-bromopyrimidine (0.0143 g, 0.090 mmol), NMP (0.7 mL), and DIPEA (0.033 mL, 0.188 mmol). The reaction mixture was then heated under microwave irradiation at 100° C. for 10 minutes. The crude reaction mixture was then allowed to cool to room temperature, diluted with methanol, filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) gave 2-{2-oxo-3-[(1-pyrimidin-2-ylpiperidin-4-yl) methyl]-2,3-dihydro-1,3-benzothiazol-6-yl}benzonitrile (11-4) as a brown solid. HRMS (M+H)$^+$: observed=428.1544, calculated=428.1540.

SCHEME 12

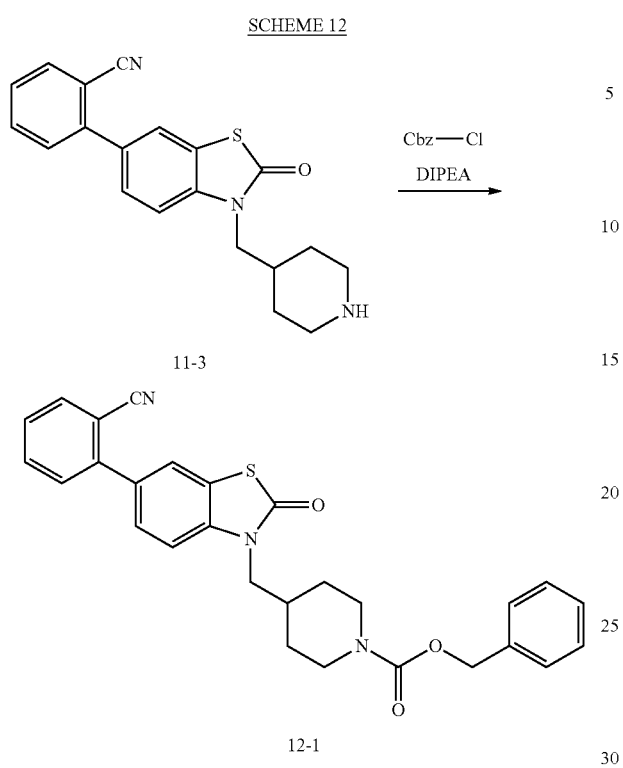

Benzyl 4-{[6-(2-cyanophenyl)-2-oxo-1,3-benzothiazol-3(2H)-yl]methyl}piperidine-1-carboxylate (12-1)

To a microwave vial was added 2-[2-oxo-3-(piperidin-4-ylmethyl)-2,3-dihydro-1,3-benzothiazol-6-yl]benzonitrile (11-3) (HCl salt) (0.025 g, 0.065 mmol), dissolved in 3 mL of anhydrous 1,4 Dioxane, then added DIPEA (0.034 mL, 0.194 mmol), followed by benzyl chloridocarbonate (0.014 mL, 0.097 mmol). The reaction mixture was then stirred at room temperature for 1 hour. The crude reaction mixture was then diluted with methanol, filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) gave benzyl 4-{[6-(2-cyanophenyl)-2-oxo-1,3-benzothiazol-3(2H)-yl]methyl}piperidine-1-carboxylate (12-1) as waxy solid. HRMS (M+H)$^+$: observed=484.1700, calculated=484.1689.

SCHEME 13

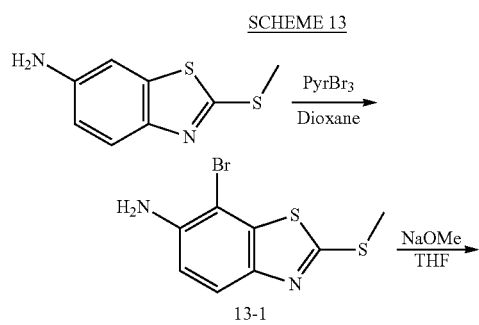

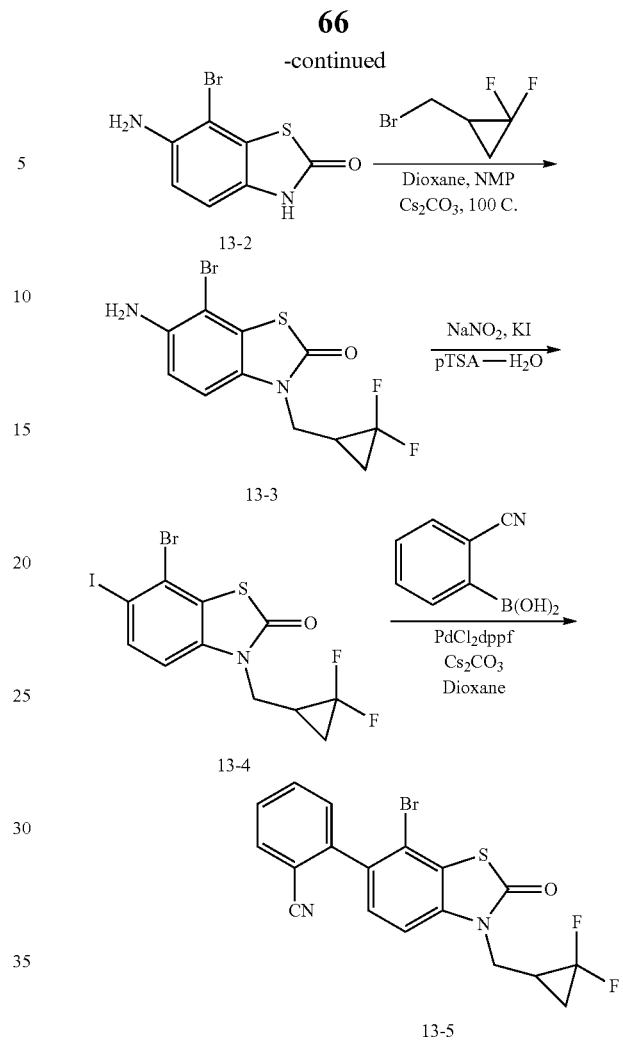

2-(7-bromo-3-{[2,2-difluorocyclopropyl]methyl}-2-oxo-2,3-dihydro-1,3-benzothiazol-6-yl)benzonitrile (13-5)

7-bromo-2-(methylthio)-1,3-benzothiazol-6-amine (13-1)

To a round bottom flask was added 2-(methylthio)-1,3-benzothiazol-6-amine (0.301 g, 1.533 mmol), Dioxane (10 mL), and pyridinium bromide perbromide (0.589 g, 1.840 mmol). The reaction mixture was then stirred at room temperature for ~5 minutes, then suspended in EtOAc, washed with sat'd Na$_2$S$_2$O$_3$, then with sat'd NaHCO$_3$, then water, then brine. Organics were then dried over Na$_2$SO$_4$ filtered & concentrated. The resulting residue was purified using silica gel chromatography (0-45% ethyl acetate/hexanes) to give 7-bromo-2-(methylthio)-1,3-benzothiazol-6-amine (13-1) as a tan solid. HRMS (M+H)$^+$: observed=274.9307, calculated=274.9307.

6-amino-7-bromo-1,3-benzothiazol-2(3H)-one (13-2)

To a round bottom flask was added 7-bromo-2-(methylthio)-1,3-benzothiazol-6-amine (13-1) (0.600 g, 2.180 mmol), THF (20 mL), and solid sodium methoxide (0.471 g, 8.72 mmol). The reaction mixture was then stirred at room temperature for several hours followed by heating to 60 C in a hot oil bath with stirring for several hours, then to 90 C for several hours. The reaction mixture was then suspended in EtOAc, washed with sat'd NaHCO₃, then water, then brine. Organics were then dried over Na₂SO₄ filtered & concentrated to give 6-amino-7-bromo-1,3-benzothiazol-2(3H)-one (13-2) as a tan solid. HRMS (M+H)⁺: observed=244.9379, calculated=244.9379.

6-amino-7-bromo-3-[(2,2-difluorocyclopropyl)methyl]-1,3-benzothiazol-2(3H)-one (13-3)

Prepared from 13-2 according to the procedures reported in Scheme 1. HRMS (M+H)⁺: observed=334.9661, calculated=334.9660.

7-bromo-3-[2,2-difluorocyclopropyl)methyl]-6-iodo-1,3-benzothiazol-2(3H)-one (13-4)

To a round bottom flask was added 6-amino-7-bromo-3-[(2,2-difluorocyclopropyl)methyl]-1,3-benzothiazol-2(3H)-one (13-3) (0.205 g, 0.612 mmol), Dioxane (2.5 mL), water (2.0 mL), potassium iodide (1.015 g, 6.12 mmol), and 4-methylbenzenesulfonic acid hydrate (0.349 g, 1.835 mmol), then dropwise addition of a solution of sodium nitrite (0.084 g, 1.223 mmol) in water (0.5 mL). Reaction mixture was then stirred at room temperature for a few hours, then heated to 75 C in a hot oil bath with stirring overnight (~15 hours). The reaction mixture was then cooled to room temperature then suspended in EtOAc, washed with sat'd Na₂S₂O₃, then with sat'd NaHCO₃, then water, then brine. Organics were then dried over Na₂SO₄ filtered & concentrated. Purification of crude reaction mixture by reverse phase chromatography (Waters Sunfire MSC18, 40% acetonitrile/0.1% trifluoroacetic acid/water→100% acetonitrile/0.1% trifluoroacetic acid/water) gave 7-bromo-3-[(2,2-difluorocyclopropyl)methyl]-6-iodo-1,3-benzothiazol-2(3H)-one (13-4) as a pink solid. HRMS (M+H)⁺: observed=445.852, calculated=445.8517.

2-(7-bromo-3-{[2,2-difluorocyclopropyl]methyl}-2-oxo-2,3-dihydro-1,3-benzothiazol-6-yl)benzonitrile (13-5)

Prepared from 13-4 according to the procedures reported in Scheme 1 except Pd(dppf)Cl₂ was used instead of bis(tri-tert-butylphosphine) palladium(0). HRMS (M+H)⁺: observed=420.9841, calculated=420.9816.

SCHEME 14

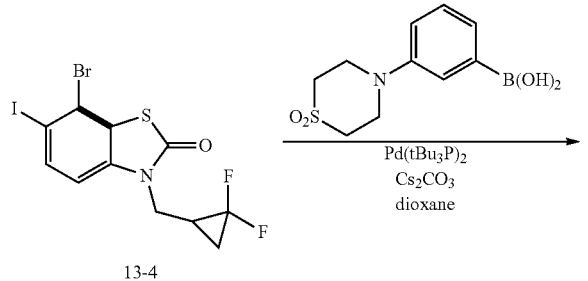

7-bromo-3-{[2,2-difluorocyclopropyl]methyl}-6-[3-(1,1-dioxidothiomorpholin-4-yl)phenyl]-1,3-benzothiazol-2(3H)-one (14-1)

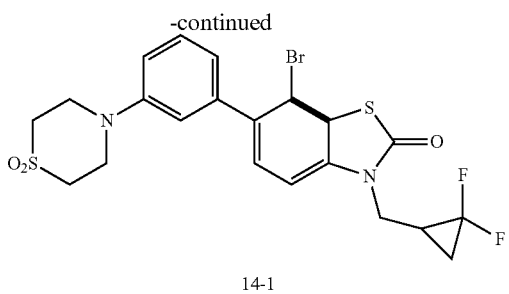

Prepared from 13-4 according to the procedures reported in Scheme 12. HRMS (M+H)⁺: observed=529.0089, calculated=529.0061.

SCHEME 15

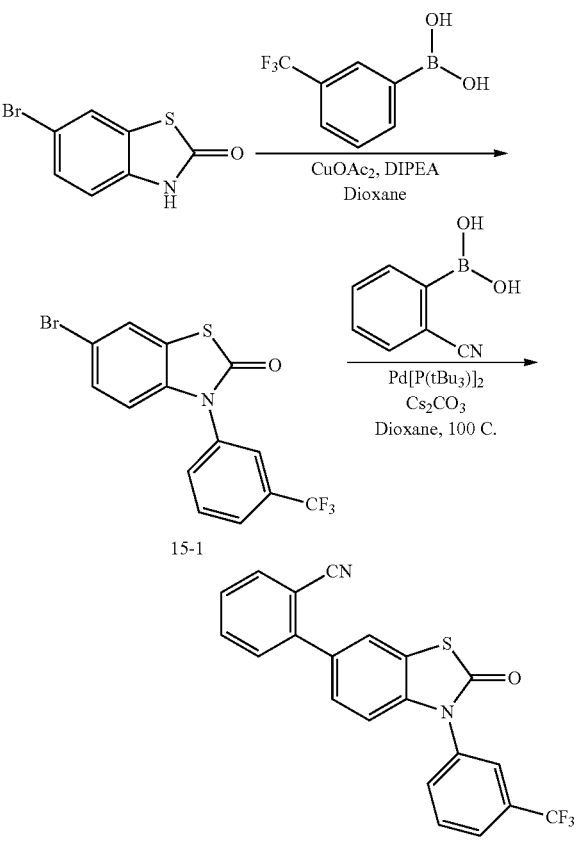

2-{2-oxo-3-[3-(trifluoromethyl)phenyl]-2,3-dihydro-1,3-benzothiazol-6-yl}benzonitrile (15-2)

6-bromo-3-[3-(trifluoromethyl)phenyl]-1,3-benzothiazol-2(3H)-one (15-1)

To a round bottom flask was added 6-bromo-1,3-benzothiazol-2(3H)-one (0.050 g, 0.217 mmol), copper(2+) diacetate (0.079 g, 0.435 mmol), [3-(trifluoromethyl)phenyl]boronic acid (0.124 g, 0.652 mmol), Dioxane (1 mL), and DIPEA (0.114 mL, 0.652 mmol). The reaction mixture was then permitted to stir open to the atmosphere for ~17 hours (overnight). The crude reaction mixture was then diluted with methanol, filtered and concentrated. Purification of crude reaction mixture by reverse phase chromatography (Waters Sunfire MSC18, 30% acetonitrile/0.1% trifluoroacetic acid/water→100% acetonitrile/0.1% trifluoroacetic acid/water) gave 6-bromo-3-[3-(trifluoromethyl)phenyl]-1,3-benzothiazol-2(3H)-one (15-1) as a white solid. HRMS (M+H)$^+$: observed=373.9455, calculated=373.9457.

2-{2-oxo-3-[3-(trifluoromethyl)phenyl]-2,3-dihydro-1,3-benzothiazol-6-yl}benzonitrile (15-2)

Prepared from 15-1 according to the procedures reported in Scheme 1. HRMS (M+H)$^+$: observed=397.0617, calculated=397.0617.

SCHEME 16

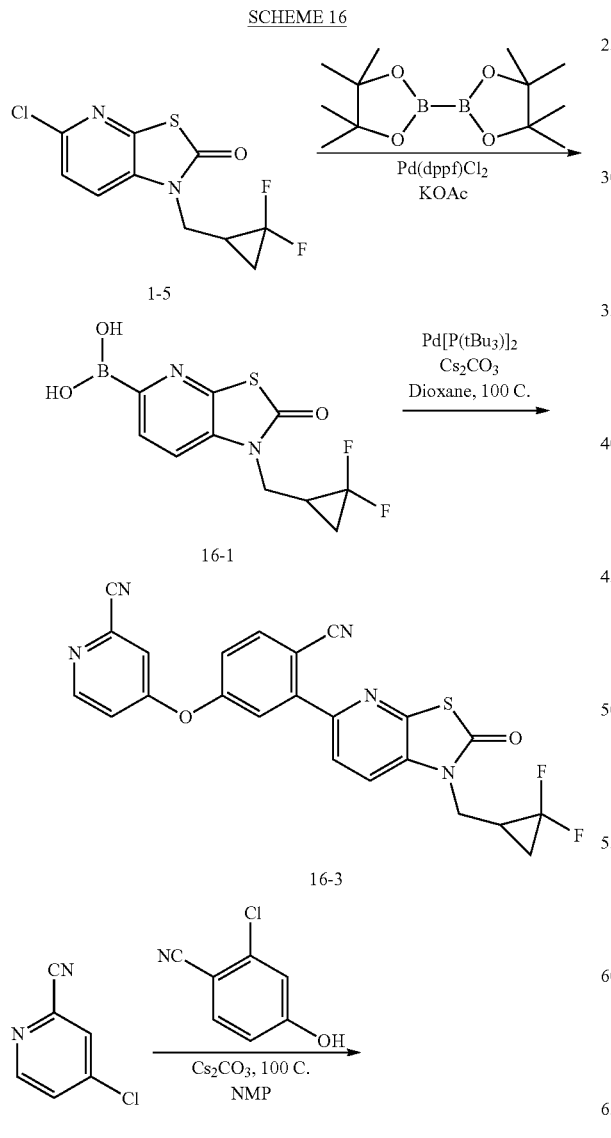

4-(4-cyano-3-{1-[(2,2-difluorocyclopropyl)methyl]-2-oxo-1,2-dihydro[1,3]thiazolo[5,4-b]pyridin-5-yl}phenoxy)pyridine-2-carbonitrile (16-3)

{1-[(2,2-difluorocyclopropyl)methyl]-2-oxo-1,2-dihydro[1,3]thiazolo[5,4-b]pyridin-5-yl}boronic acid (16-1)

Prepared from 1-5 according to the procedures reported in Scheme 2. MS (M+H)$^+$: observed=287.1, calculated=287.063.

4-(3-chloro-4-cyanophenoxy)pyridine-2-carbonitrile (16-2)

To a microwave vial was added 4-chloropyridine-2-carbonitrile (3.14 g, 22.63 mmol), 2-chloro-4-hydroxybenzonitrilem (3.31 g, 21.55 mmol), cesium carbonate (14.05 g, 43.1 mmol), and NMP (10 mL). The reaction mixture was then heated under microwave irradiation at 100° C. for 20 minutes. The crude reaction mixture was then allowed to cool to room temperature, diluted with EtOAc (50 mL) & water (50 mL), then filtered to give 4-(3-chloro-4-cyanophenoxy)pyridine-2-carbonitrile (16-2) as a tan solid. MS (M+H)$^+$: observed=256.0, calculated=256.7.

4-(4-cyano-3-{1-[(2,2-difluorocyclopropyl)methyl]-2-oxo-1,2-dihydro[1,3]thiazolo[5,4-b]pyridin-5-yl}phenoxy)pyridine-2-carbonitrile (16-3)

Prepared from 16-1 and 16-2 according to the procedures reported in Scheme 1. $^1$H NMR (400 MHz, CD$_3$OD): δ 8.63 (s, 1H); 8.02 (s, 1H); 7.92 (s, 1H); 7.82 (d, J=7.2 Hz, 1H); 7.73 (d, J=5.4 Hz, 1H); 7.65 (s, 1H); 7.42 (s, 1H); 7.33 (s, 1H); 4.22 (d, J=45.7 Hz, 2H); 2.23 (s, 1H); 1.62 (s, 1H); 1.45 (s, 1H). HRMS (M+H)$^+$: observed=462.0829, calculated=462.0831.

SCHEME 17

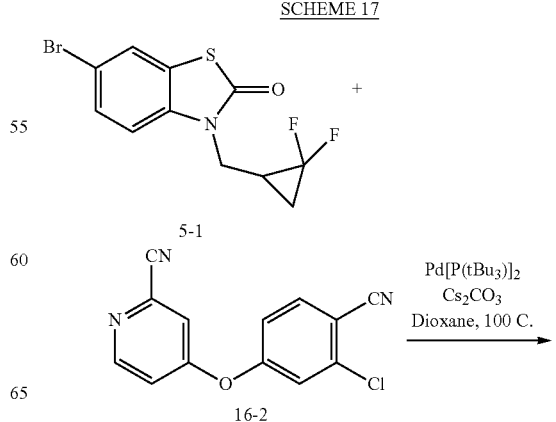

-continued

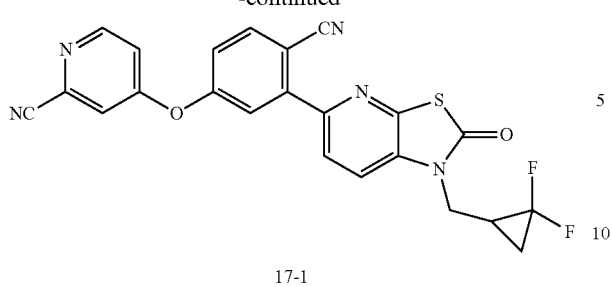

17-1

4-(4-cyano-3-{1-[(2,2-difluorocyclopropyl)methyl]-2-oxo-1,2-dihydro[1,3]thiazolo[5,4-b]pyridin-5-yl}phenoxy)pyridine-2-carbonitrile (17-1)

Prepared from 5-1 and 16-2 according to the procedures reported in Scheme 1. HRMS (M+H)+: observed=462.0829, calculated=462.0831.

SCHEME 18

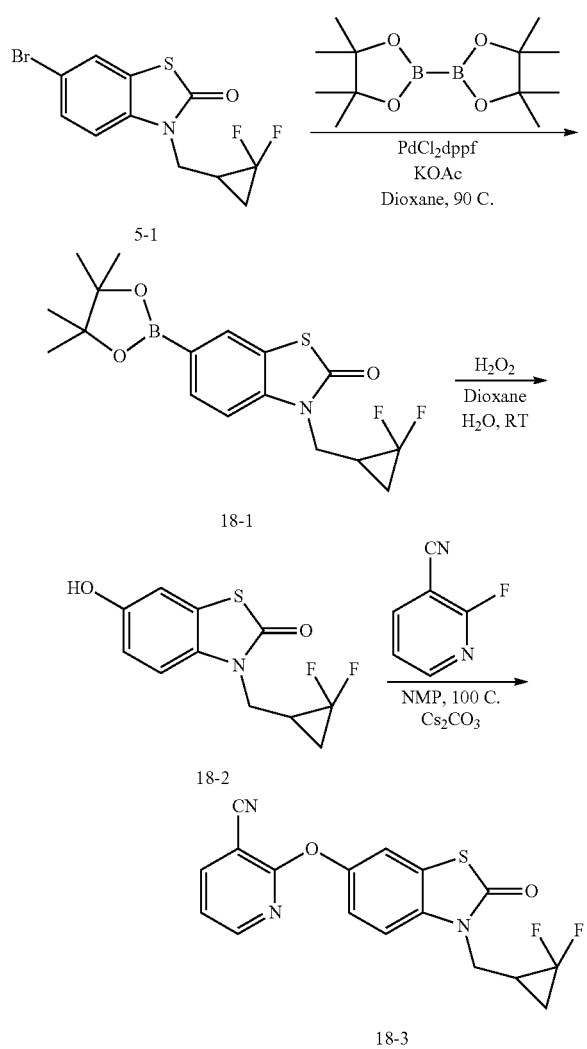

2-({3-[(2,2-difluorocyclopropyl)methyl]-2-oxo-2,3-dihydro-1,3-benzothiazol-6-yl}oxy)nicotinonitrile (18-3)

3-[(2,2-difluorocyclopropyl)methyl]-6-(4,4,5,5-tetramethyl-1,3,2-dioxaborolan-2-yl)-1,3-benzothiazol-2(3H)-one (18-1)

To a round bottom flask was added 6-bromo-3-[(2,2-difluorocyclopropyl) methyl]-1,3-benzothiazol-2(3H)-one (5-1) (5.32 g, 16.6 mmol), potassium acetate (7.40 g, 75.0 mmol), 4,4,4',4',5,5'-hexamethyl-2,2'-bi-1,3,2-dioxaborolane (4.85 g, 6.93 mmol), bis(diphenylphosphino)ferrocene dicholoropalladium (2.75 g, 3.37 mmol), followed by anhydrous 1,4-dioxane (100 mL). The reaction mixture was then heated to 90° C. while stirring in a hot oil bath with a water cooled reflux condenser attached under an atmosphere of nitrogen for 18 hours. The crude reaction mixture was cooled to room temperature, then suspended in ethyl acetate and washed with a saturated solution of sodium bicarbonate, followed by water, then brine, dried over sodium sulfate, filtered, and concentrated. The resulting residue was then purified by silica gel chromatography (0-25% EtOAc/Hex) to give 3-[(2,2-difluorocyclopropyl) methyl]-6-(4,4,5,5-tetramethyl-1,3,2-dioxaborolan-2-yl)-1,3-benzothiazol-2(3H)-one (18-1) as a tan solid. MS (M+H)$^+$: observed=368.2, calculated=368.2.

3-[(2,2-difluorocyclopropyl)methyl]-6-hydroxy-1,3-benzothiazol-2(3H)-one (18-2)

To a solution of 3-[(2,2-difluorocyclopropyl)methyl]-6-(4,4,5,5-tetramethyl-1,3,2-dioxaborolan-2-yl)-1,3-benzothiazol-2(3H)-one (18-1) (0.483 g, 1.32 mmol) in anhydrous 1,4-dioxane (5 mL) was added a 30% by weight solution of hydrogen peroxide in water (0.537 mL, 5.26 mmol. The reaction mixture was then stirred at room temperature for 0.5 hours. The crude reaction mixture was diluted with methanol and NMP, filtered and concentrated. Purification of crude reaction mixture by reverse phase chromatography (Waters Sunfire MSC18, 5% acetonitrile/0.1% trifluoroacetic acid/water→95% acetonitrile/0.1% trifluoroacetic acid/water) gave 3-[2,2-difluorocyclopropyl)methyl]-6-hydroxy-1,3-benzothiazol-2(3H)-one (18-2) as a tan solid. HRMS (M+H)$^+$: observed=258.0396, calculated=258.0395.

2-[(3-{[2,2-difluorocyclopropyl]methyl}-2-oxo-2,3-dihydro-1,3 benzothiazol-6-yl)oxy]pyridine-3-carbonitrile (18-3)

To a solution of 3-[(2,2-difluorocyclopropyl)methyl]-6-hydroxy-1,3-benzothiazol-2(3H)-one (18-2) (0.033 g, 0.13 mmol) in anhydrous NMP (1 mL) was added cesium carbonate (0.084 g, 0.26 mmol) and 2-fluoronicotinonitrile (0.024 g, 0.19 mmol). The reaction mixture was then heated under microwave irradiation at 100° C. for 10 minutes. The crude reaction mixture was then allowed to cool to room temperature, diluted with methanol and NMP, then filtered and concentrated. Purification of crude reaction mixture by reverse phase chromatography (Waters Sunfire MSC18, 10% acetonitrile/0.1% trifluoroacetic acid/water→100% acetonitrile/ 0.1% trifluoroacetic acid/water) gave 2-[(3-{[2,2-difluorocyclopropyl]methyl}-2-oxo-2,3-dihydro-1,3-benzothiazol-6-yl)oxy]pyridine-3-carbonitrile (18-3) as an off-white solid. HRMS (M+H)$^+$: observed=360.0623, calculated=360.0613.

TABLE 10

The following compound was prepared from 18-2 by a reaction sequence analogous to that illustrated in Scheme 1.

| Cmpd | Structure | IUPAC Name | Exact Mass (M + H) |
|---|---|---|---|
| 18-4 | 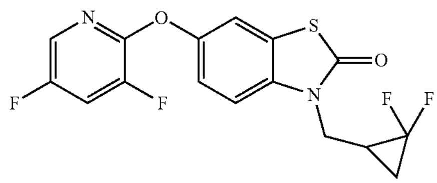 [SMILES: O=c1sc2cc(Oc3ncc(F)cc3F)ccc2n1CC1CC1(F)F] | 3-{[2,2-difluorocyclopropyl]methyl}-6-[(3,5-difluoropyridin-2-yl)oxy]-1,3-benzothiazol-2(3H)-one | Calc'd 371.0472, found 371.0474 |
| 18-5 | 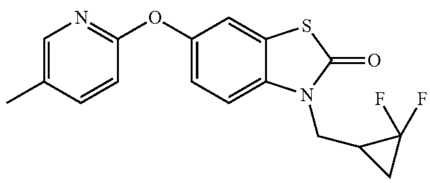 [SMILES: Cc1ccc(Oc2ccc3c(c2)sc(=O)n3CC2CC2(F)F)nc1] | 3-{[2,2-difluorocyclopropyl]methyl}-6-[(5-methylpyridin-2-yl)oxy]-1,3-benzothiazol-2(3H)-one | Calc'd 349.0817, found 349.0818 |
| 18-6 | 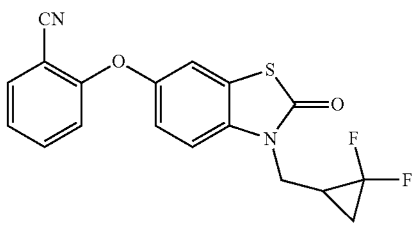 [SMILES: N#Cc1ccccc1Oc1ccc2c(c1)sc(=O)n2CC1CC1(F)F] | 2-[(3-{[2,2-difluorocyclopropyl]methyl}-2-oxo-2,3-dihydro-1,3-benzothiazol-6-yl)oxy]benzonitrile | Calc'd 359.066, found 359.0665 |
| 18-7 | 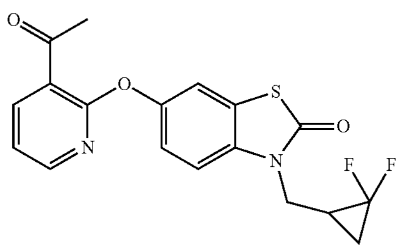 [SMILES: CC(=O)c1cccnc1Oc1ccc2c(c1)sc(=O)n2CC1CC1(F)F] | 6-[(3-acetylpyridin-2-yl)oxy]-3-{[2,2-difluorocyclopropyl]methyl}-1,3-benzothiazol-2(3H)-one | Calc'd 377.0766, found 377.0769 |
| 18-8 | 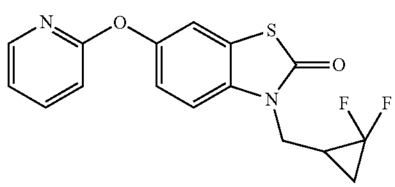 [SMILES: O=c1sc2cc(Oc3ccccn3)ccc2n1CC1CC1(F)F] | 3-{[2,2-difluorocyclopropyl]methyl}-6-(pyridin-2-yloxy)-1,3-benzothiazol-2(3H)-one | Calc'd 335.0660, found 335.0661 |
| 18-9 | 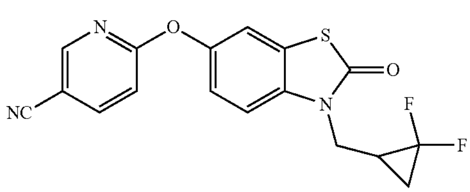 [SMILES: N#Cc1ccc(Oc2ccc3c(c2)sc(=O)n3CC2CC2(F)F)nc1] | 6-[(3-{[2,2-difluorocyclopropyl]methyl}-2-oxo-2,3-dihydro-1,3-benzothiazol-6-yl)oxy]pyridine-3-carbonitrile | Calc'd 360.0613, found 360.0620 |
| 18-10 | 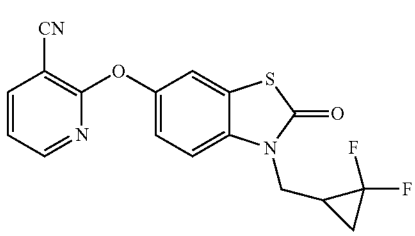 | 2-[(3-{[2,2-difluorocyclopropyl]methyl}-2-oxo-2,3-dihydro-1,3-benzothiazol-6-yl)oxy]pyridine-3-carbonitrile | Calc'd 360.0613, found 360.0623 |

TABLE 10-continued

The following compound was prepared from 18-2 by a reaction sequence analogous to that illustrated in Scheme 1.

| Cmpd | Structure | IUPAC Name | Exact Mass (M + H) |
|---|---|---|---|
| 18-11 | 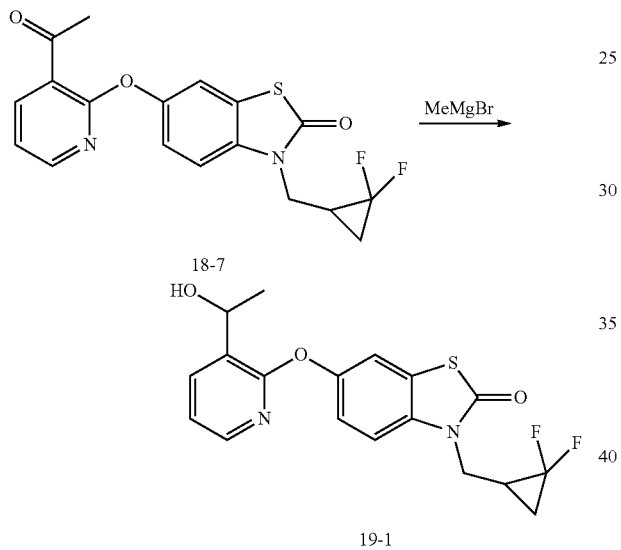 | 2-[(3-{[2,2-difluorocyclopropyl]methyl}-2-oxo-2,3-dihydro-1,3-benzothiazol-6-yl)oxy]-3-fluorobenzonitrile | Calc'd 377.0566, found 377.0574 |

SCHEME 19

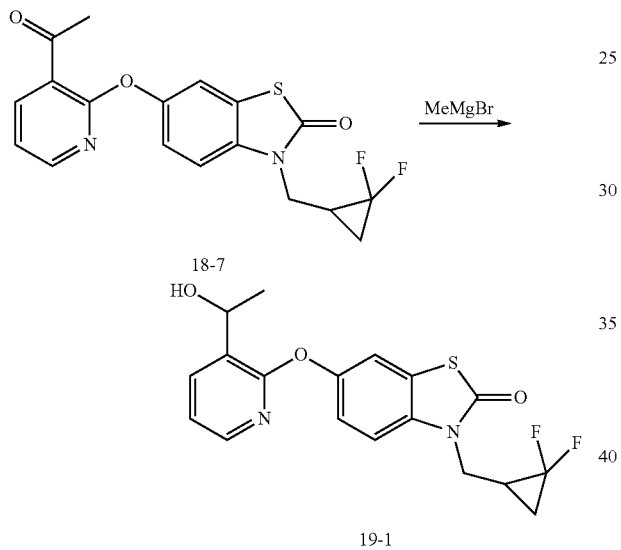

3-[(2,2-difluorocyclopropyl)methyl]-6-{[3-(1-hydroxyethyl)pyridin-2-yl]oxy}-1,3-benzothiazol-2(3H)-one (19-1)

Prepared from 18-7 according to the procedures reported in Scheme 2. HRMS (M+H)+: observed=379.0916, calculated=379.0922.

What is claimed is:
1. A compound according to Formula I

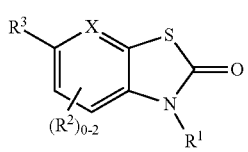

wherein:
R$^1$ is selected from the group consisting of —(CH$_2$)$_p$cyclopropyl, —(CH$_2$)$_p$cyclopentyl, —(CH$_2$)$_p$cyclohexyl, —(CH$_2$)$_p$piperidinyl, (CH$_2$)$_p$phenyl, and C$_{1-6}$ alkyl, wherein each said cyclopropyl, cyclopentyl, cyclohexyl and alkyl is optionally substituted with 1-3 halo, C$_{1-6}$ alkyl, CF$_3$, —C(O)OC$_{1-6}$ alkyl, pyrimidinyl, 2,2-dimethylpropyl and 4,4,4-trifluorobutyl;

X represents —CR$^b$—, or —N—;

each R$^2$ is independently selected from the group consisting of: hydrogen, halo, OH, C$_{1-4}$alkyl, C$_{1-4}$alkoxy, CF$_3$ and —CN;

R$^3$ is selected from the group consisting of phenyl, pyridyl, —O-phenyl, and —O-pyridyl, wherein each said phenyl, pyridyl, —O-phenyl, and —O-pyridyl are optionally substituted with 1 to 3 R$^a$ groups;

each R$^a$ is independently selected from the group consisting of:
(1) halo,
(2) C$_{1-8}$alkyl,
(3) C$_{2-6}$alkenyl,
(4) C$_{2-6}$alkynyl,
(5) C$_{3-6}$cycloalkyl,
(6) C$_{1-6}$alkoxy,
(7) C$_{3-6}$cycloalkoxy,
(8) —CN,
(9) —OH,
(10) —C(O)—O—R,
(11) —C(O)—C$_{1-6}$alkyl,
(12) —N(R)$_2$,
(13) —C(O)—N(R)$_2$,
(14) —S(O)$_k$—C$_{1-6}$alkyl, wherein k is 0, 1 or 2,
(15) —(CH$_2$)pC$_{6-10}$aryl,
(16) —(CH$_2$)pC$_{5-10}$heterocyclyl,
(17) CF$_3$,
(18) —C(O)-aryl,
(19) —N(R)-aryl,
(20) benzyl,
(21) benzyloxy,
(22) phenoxy,
(23) —C(CH$_3$)$_2$OR,
(24) —SH,
(25) —SO$_2$N(R)R,
(26) —(CH$_2$)$_p$N(R)C(O)N(R)R,
(27) —(CH$_2$)pN(R)C(O)C$_{1-6}$alkyl,
(28) —(CH$_2$)pN(R)SO$_2$N(R)R, and
(29) —B(OH)$_2$,
(30) —OR,
(31) —(CH$_2$)$_p$NHC(O)OC$_{1-6}$alkyl,
(32) —OC$_{5-10}$heterocyclyl, wherein groups (2) to (7), (11), (14) to (16), (18) to (23), and (32) above are optionally substituted with one up to the maximum number of substitutable positions of one or more substituents independently selected from the group consisting of: OH, CN, halo, carboxy, —C(O)—O—$C_{1-4}$alkyl, $C_{1-4}$alkyl, $C_{1-4}$alkoxy, $C_{1-4}$alkylamino, phenyl and C5-10 heterocycle, R is selected from the group consisting of: H, $(CH_2)_pC_{6-10}$aryl and $C_{1-6}$alkyl;

$R^b$ and $R^k$ independently represent H or halo;

p represents 0-1;

and pharmaceutically acceptable salts thereof.

2. The compound according to claim 1 wherein $R^1$ is —$(CH_2)_p$cyclopropyl, said cyclopropyl optionally substituted with 0-2 groups of halo.

3. The compound according to claim 1 wherein $R^1$ is optionally substituted $C_{1-6}$ alkyl.

4. The compound according to claim 1 wherein $R^a$ is selected from the group consisting of: halo, $C_{1-8}$alkyl, $C_{3-6}$cycloalkyl, —$OC_{5-10}$heterocyclyl, $C_{1-6}$alkoxy, $C_{3-6}$cycloalkoxy, —CN, —OH, —C(O)—$C_{1-6}$alkyl, —$(CH_2)pC_{6-10}$aryl, —$(CH_2)pC_{5-10}$heterocyclyl, $CF_3$, —C(O)-aryl, and —$(CH_2)pNHC(O)OC_{1-6}$alkyl, said alkyl, aryl and heterocyclyl optionally substituted with 1 to 3 groups of OH, CN, halo, carboxy, —C(O)—O—$C_{1-4}$alkyl, $C_{1-4}$alkyl, $C_{1-4}$alkoxy, $C_{1-4}$alkylamino, phenyl and $C_{5-10}$ heterocycle.

5. The compound according to claim 1 wherein $R^3$ is C6-10 aryl, C5-10 heterocyclyl, $OC6-_{10}$ aryl or $OC_{5-10}$ heterocyclyl optionally substituted with 1 to 3 substituents $R^a$.

6. The compound according to claim 5 wherein $R^3$ is optionally substituted phenyl or O-phenyl.

7. The compound according to claim 5 wherein $R^3$ is optionally substituted pyridyl or O-pyridyl.

8. The compound according to claim 1 represented by Formula Ia

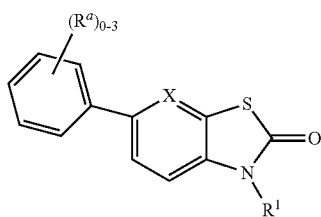

wherein X is —CH— or —N, $R^1$ is selected from —$(CH_2)_p$cyclopropyl, —$(CH_2)_p$cyclopentyl, —$(CH_2)_p$cyclohexyl, —$(CH_2)_p$piperidinyl, $(CH_2)_p$phenyl, and $C_{1-6}$ alkyl, said cyclopropyl, cyclopentyl, cyclohexyl, piperidinyl, phenyl, and alkyl optionally substituted with 1-3 halo, $C_{1-6}$ alkyl, $CF_3$, —$C(O)OC_{1-6}$ alkyl, pyrimidinyl, 2,2-dimethylpropyl and 4,4,4-trifluorobutyl; $R^a$ is selected from the group consisting of CN, halo, OR, $CF_3$, —$C(CH_3)_2OR$, $C_{1-6}$ alkyl, $(CH_2)_p$morpholinyl, $(CH_2)_p$dioxidomorpholinyl, and $(CH_2)_pNHC(O)OC(CH_3)_3$ and pharmaceutically acceptable salts thereof.

9. The compound according to claim 1 represented by Formula Ib

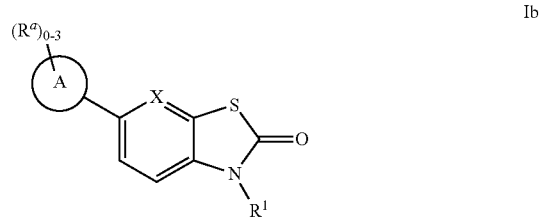

wherein X is —CH— or —N, A is pyridyl and $R^1$ is selected from —$(CH_2)_p$cyclopropyl, —$(CH_2)_p$cyclopentyl, —$(CH_2)_p$cyclohexyl, —$(CH_2)_p$piperidinyl, $(CH_2)_p$phenyl, and $C_{1-6}$ alkyl, said cyclopropyl, cyclopentyl, cyclohexyl, piperidinyl, phenyl, and alkyl optionally substituted with 1-3 halo, $C_{1-6}$ alkyl, $CF_3$, —$C(O)OC_{1-6}$ alkyl, pyrimidinyl, 2,2-dimethylpropyl and 4,4,4-trifluorobutyl; and $R^a$ is selected from the group consisting of CN, halo, OR, $CF_3$, —$C(CH_3)_2OR$, C1-6 alkyl, $(CH_2)_p$morpholinyl, $(CH_2)_p$dioxidomorpholinyl, and $(CH_2)_pNHC(O)OC(CH_3)_3$ and pharmaceutically acceptable salts thereof.

10. The compound according to claim 1 represented by Formula Ic

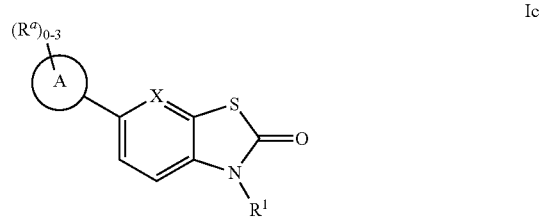

wherein X is —CH— or —N, A is O-phenyl or O-pyridyl and $R^1$ is selected from —$(CH_2)_p$cyclopropyl, —$(CH_2)_p$cyclopentyl, —$(CH_2)_p$cyclohexyl, —$(CH_2)_p$piperidinyl, $(CH_2)_p$phenyl, and $C_{1-6}$ alkyl, said cyclopropyl, cyclopentyl, cyclohexyl, piperidinyl, phenyl, and alkyl optionally substituted with 1-3 halo, $C_{1-6}$ alkyl, $CF_3$, —$C(O)OC_{1-6}$ alkyl, pyrimidinyl, 2,2-dimethylpropyl and 4,4,4-trifluorobutyl; $R^a$ is selected from the group consisting of CN, halo, OR, $CF_3$, —$C(CH_3)_2OR$, C1-6 alkyl, $(CH_2)_p$morpholinyl, $(CH_2)_p$dioxidomorpholinyl, and $(CH_2)_pNHC(O)OC(CH_3)_3$ and pharmaceutically acceptable salts thereof.

11. A compound which is:
   2-(1-{[2,2-difluorocyclopropyl]methyl}-2-oxo-1,2-dihydro[1,3]thiazolo[5,4-b]pyridin-5-yl)benzonitrile,
   1-{[2,2-difluorocyclopropyl]methyl}-5-[3-(1,1-dioxidothiomorpholin-4-yl)phenyl][1,3]thiazolo[5,4-b]pyridin-2(1H)-one,
   1-{[2,2-difluorocyclopropyl]methyl}-5-(2-methylphenyl)[1,3]thiazolo[5,4-b]pyridin-2(1H)-one,
   3-(1-{[2,2-difluorocyclopropyl]methyl}-2-oxo-1,2-dihydro[1,3]thiazolo[5,4-b]pyridin-5-yl)pyridine-4-carbonitrile,
   2-(1-{[2,2-difluorocyclopropyl]methyl}-2-oxo-1,2-dihydro[1,3]thiazolo[5,4-b]pyridin-5-yl)-5-fluorobenzonitrile,
   1-[(2,2-difluorocyclopropyl)methyl]-5-phenyl[1,3]thiazolo[5,4-b]pyridin-2(1H)-one, 5-{5-[(4-acetylpiperazin-1-yl)methyl]-2-methyl phenyl}-1-[(2,2-difluorocyclopropyl)methyl][1,3]thiazolo[5,4-b]pyridin-2(1H)-one, 1-{[2,2-difluorocyclopropyl]methyl}-5-[5-(1-hydroxy-1-methylethyl)-2-methylphenyl][1,3]thiazolo[5,4-b]pyridin-2(1H)-one, 2-[1-(2,2-dimethylpropyl)-2-oxo-1,2-dihydro[1,3]thiazolo[5,4-b]pyridin-5-yl]benzonitrile, 1-(2,2-dimethylpropyl)-5-[5-(1-hydroxy-1-methylethyl)-2-methylphenyl][1,3]thiazolo[5,4-b]pyridin-2(1H)-one, 1-(2,2-dimethylpropyl)-5-[3-(1,1-dioxidothiomorpholin-4-yl)phenyl][1,3]thiazolo[5,4-b]pyridin-2(1H)-one, 2-[1-(cyclopropylmethyl)-2-oxo-1,2-dihydro[1,3]thiazolo[5,4-b]pyridin-5-yl]benzonitrile, 1-(cyclopropylmethyl)-5-[3-(1,1-dioxidothiomorpholin-4-yl)phenyl][1,3]thiazolo[5,4-b]pyridine-2(1H)-one, 2-(3-{[2,2-difluorocyclopropyl]methyl}-2-oxo-2,3-dihydro-1,3-benzothiazol-6-yl)benzonitrile, 3-(3-{[2,2-difluorocyclopropyl]methyl}-2-oxo-2,3-dihydro-1,3-benzothiazol-6-yl)pyridine-4-carbonitrile, 3-{[2,2-difluorocyclopropyl]methyl}-6-(2,3-dihydro-1-benzofuran-5-yl)-1,3-benzothiazol-2(3H)-one, 2-(3-{[2,2-difluorocyclopropyl]methyl}-2-oxo-2,3-dihydro-1,3-benzothiazol-6-yl)-6-methylpyridine-3-carbonitrile, 2-(3-{[2,2-difluorocyclopropyl]methyl}-2-oxo-2,3-dihydro-1,3-benzothiazol-6-yl)pyridine-3-carbonitrile, 3-{[2,2-difluorocyclopropyl]methyl}-6-(2-fluoro-5-methylpyridin-3-yl)-1,3-benzothiazol-2(3H)-one, 3-{[2,2-difluorocyclopropyl]methyl}-6-[3-(1-hydroxy-1-methylethyl)phenyl]-1,3-benzothiazol-2(3H)-one, 3-{[2,2-difluorocyclopropyl]methyl}-6-[4-(1,1-dioxidothiomorpholin-4-yl)phenyl]-1,3-benzothiazol-2(3H)-one, 3-(3-{[2,2-difluorocyclopropyl]methyl}-2-oxo-2,3-dihydro-1,3-benzothiazol-6-yl)-4-fluorobenzonitrile, 4-(3-{[2,2-difluorocyclopropyl]methyl}-2-oxo-2,3-dihydro-1,3-benzothiazol-6-yl)pyridine-3-carbonitrile, 2-(3-{[2,2-difluorocyclopropyl]methyl}-2-oxo-2,3-dihydro-1,3-benzothiazol-6-yl)-5-fluorobenzonitrile, 2-(3-{[2,2-difluorocyclopropyl]methyl}-2-oxo-2,3-dihydro-1,3-benzothiazol-6-yl)-6-fluorobenzonitrile, tert-butyl [3-(3-{[2,2-difluorocyclopropyl]methyl}-2-oxo-2,3-dihydro-1,3-benzothiazol-6-yl)benzyl]carbamate, 2-(3-{[2,2-difluorocyclopropyl]methyl}-2-oxo-2,3-dihydro-1,3-benzothiazol-6-yl)-3-fluorobenzonitrile, 3-{[2,2-difluorocyclopropyl]methyl}-6-[3-(morpholin-4-ylmethyl)phenyl]-1,3-benzothiazol-2(3H)-one, 3-{[2,2-difluorocyclopropyl]methyl}-6-[3-(1,1-dioxidothiomorpholin-4-yl)phenyl]-1,3-benzothiazol-2(3H)-one, 2-(3-{[2,2-difluorocyclopropyl]methyl}-2-oxo-2,3-dihydro-1,3-benzothiazol-6-yl)-3,4-difluorobenzonitrile, 3-{[2,2-difluorocyclopropyl]methyl}-6-(2,3-difluorophenyl)-1,3-benzothiazol-2(3H)-one, 3-(3-{[2,2-difluorocyclopropyl]methyl}-2-oxo-2,3-dihydro-1,3-benzothiazol-6-yl)pyrazine-2-carbonitrile, 2-(3-{[2,2-difluorocyclopropyl]methyl}-2-oxo-2,3-dihydro-1,3-benzothiazol-6-yl)-4-fluorobenzonitrile, 2-(3-{[2,2-difluorocyclopropyl]methyl}-2-oxo-2,3-dihydro-1,3-benzothiazol-6-yl)-4-(morpholin-4-ylmethyl)benzonitrile, 3-{[2,2-difluorocyclopropyl]methyl}-6-(2,5-difluorophenyl)-1,3-benzothiazol-2(3H)-one, 3-{[2,2-difluorocyclopropyl]methyl}-6-(2,6-difluorophenyl)-1,3-benzothiazol-2(3H)-one, 3-{[2,2-difluorocyclopropyl]methyl}-6-(2-fluorophenyl)-1,3-benzothiazol-2(3H)-one, 3-{[2,2-difluorocyclopropyl]methyl}-6-(2,4-difluorophenyl)-1,3-benzothiazol-2(3H)-one, 2-(3-{[2,2-difluorocyclopropyl]methyl}-2-oxo-2,3-dihydro-1,3-benzothiazol-6-yl)-3,6-difluorobenzonitrile, 3-{[2,2-difluorocyclopropyl]methyl}-6-[5-(1-hydroxy-1-methylethyl)-2-methylphenyl]-1,3-benzothiazol-2(3H)-one, 2-[3-(cyclopropylmethyl)-2-oxo-2,3-dihydro-1,3-benzothiazol-6-yl]benzonitrile, 3-(cyclopropylmethyl)-6-phenyl-1,3-benzothiazol-2(3H)-one, 3-[3-(cyclopropylmethyl)-2-oxo-2,3-dihydro-1,3-benzothiazol-6-yl]benzonitrile, 3-[3-(cyclopropylmethyl)-2-oxo-2,3-dihydro-1,3-benzothiazol-6-yl]pyridine-4-carbonitrile, 2-[3-(cyclopropylmethyl)-2-oxo-2,3-dihydro-1,3-benzothiazol-6-yl]-5-fluorobenzonitrile, 2-[3-(cyclopropylmethyl)-2-oxo-2,3-dihydro-1,3-benzothiazol-6-yl]-3-methoxybenzonitrile, 2-[3-(cyclopropylmethyl)-2-oxo-2,3-dihydro-1,3-benzothiazol-6-yl]-6-methoxybenzonitrile, 3-[3-(cyclopropylmethyl)-2-oxo-2,3-dihydro-1,3-benzothiazol-6-yl]-4-fluorobenzonitrile, 3-(cyclopropylmethyl)-6-(2-fluorophenyl)-1,3-benzothiazol-2(3H)-one, 2-[3-(cyclopropylmethyl)-2-oxo-2,3-dihydro-1,3-benzothiazol-6-yl]-5-(trifluoromethyl)benzonitrile, 2-[3-(cyclopropylmethyl)-2-oxo-2,3-dihydro-1,3-benzothiazol-6-yl]-6-(trifluoromethyl)benzonitrile, 3-(cyclopropylmethyl)-6-(2,5-difluorophenyl)-1,3-benzothiazol-2(3H)-one, 3-(cyclopropylmethyl)-6-(2-methoxyphenyl)-1,3-benzothiazol-2(3H)-one, 3-(cyclopropylmethyl)-6-(2-methylphenyl)-1,3-benzothiazol-2(3H)-one, 3-(cyclopropylmethyl)-6-[3-(1,1-dioxidothiomorpholin-4-yl)phenyl]-1,3-benzothiazol-2(3H)-one, 2-[3-(2,2-dimethylpropyl)-2-oxo-2,3-dihydro-1,3-benzothiazol-6-yl]benzonitrile, 3-(2,2-dimethylpropyl)-6-phenyl-1,3-benzothiazol-2(3H)-one, 3-[3-(2,2-dimethylpropyl)-2-oxo-2,3-dihydro-1,3-benzothiazol-6-yl]benzonitrile, 3-(2,2-dimethylpropyl)-6-[3-(1,1-dioxidothiomorpholin-4-yl)phenyl]-1,3-benzothiazol-2(3H)-one, 3-butyl-6-phenyl-1,3-benzothiazol-2(3H)-one, 3-(cyclopentylmethyl)-6-phenyl-1,3-benzothiazol-2(3H)-one, 2-(2-oxo-3-propyl-2,3-dihydro-1,3-benzothiazol-6-yl)benzonitrile, 2-[2-oxo-3-(3,3,3-trifluoropropyl)-2,3-dihydro-1,3-benzothiazol-6-yl]benzonitrile, 2-(3-butyl-2-oxo-2,3-dihydro-1,3-benzothiazol-6-yl)benzonitrile, 2-(2-oxo-3-pentyl-2,3-dihydro-1,3-benzothiazol-6-yl)benzonitrile, 2-(3-hexyl-2-oxo-2,3-dihydro-1,3-benzothiazol-6-yl)benzonitrile, 2-[3-(2-methylpropyl)-2-oxo-2,3-dihydro-1,3-benzothiazol-6-yl]benzonitrile, 2-[2-oxo-3-(4,4,4-trifluorobutyl)-2,3-dihydro-1,3-benzothiazol-6-yl]benzonitrile, 2-[3-(cyclobutylmethyl)-2-oxo-2,3-dihydro-1,3-benzothiazol-6-yl]benzonitrile,
2-[3-(cyclopentylmethyl)-2-oxo-2,3-dihydro-1,3-benzothiazol-6-yl]benzonitrile,
2-[3-(cyclohexylmethyl)-2-oxo-2,3-dihydro-1,3-benzothiazol-6-yl]benzonitrile,
2-[3-(4-tert-butylbenzyl)-2-oxo-2,3-dihydro-1,3-benzothiazol-6-yl]benzonitrile,
2-{3-[2-fluoro-5-(trifluoromethyl)benzyl]-2-oxo-2,3-dihydro-1,3-benzothiazol-6-yl}benzonitrile,
2-[3-(4-bromo-2-fluorobenzyl)-2-oxo-2,3-dihydro-1,3-benzothiazol-6-yl]benzonitrile,
[3-(4-chloro-2-fluorobenzyl)-2-oxo-2,3-dihydro-1,3-benzothiazol-6-yl]benzonitrile,
2-[3-(4-methoxybenzyl)-2-oxo-2,3-dihydro-1,3-benzothiazol-6-yl]benzonitrile,
2-[3-(1-cyclopropylethyl)-2-oxo-2,3-dihydro-1,3-benzothiazol-6-yl]benzonitrile,
2-{3-[1,2-dimethylpropyl]-2-oxo-2,3-dihydro-1,3-benzothiazol-6-yl}benzonitrile,
2-{3-[1-cyclopentylethyl]-2-oxo-2,3-dihydro-1,3-benzothiazol-6-yl}benzonitrile,
2-{3-[1-cyclohexylethyl]-2-oxo-2,3-dihydro-1,3-benzothiazol-6-yl}benzonitrile,
2-{3-[1-methylbutyl]-2-oxo-2,3-dihydro-1,3-benzothiazol-6-yl}benzonitrile,
2-{3-[(1-methylcyclopropyl)methyl]-2-oxo-2,3-dihydro-1,3-benzothiazol-6-yl}benzonitrile,
2-{2-oxo-3-[(1-pyrimidin-2-ylpiperidin-4-yl)methyl]-2,3-dihydro-1,3-benzothiazol-6-yl}benzonitrile,
2-[2-oxo-3-(piperidin-4-ylmethyl)-2,3-dihydro-1,3-benzothiazol-6-yl]benzonitrile,
Benzyl 4-{[6-(2-cyanophenyl)-2-oxo-1,3-benzothiazol-3(2H)-yl]methyl}piperidine-1-carboxylate,
2-(7-bromo-3-{[2,2-difluorocyclopropyl]methyl}-2-oxo-2,3-dihydro-1,3-benzothiazol-6-yl)benzonitrile,
7-bromo-3-{[2,2-difluorocyclopropyl]methyl}-6-[3-(1,1-dioxidothiomorpholin-4-yl)phenyl]-1,3-benzothiazol-2(3H)-one,
2-{2-oxo-3-[3-(trifluoromethyl)phenyl]-2,3-dihydro-1,3-benzothiazol-6-yl}benzonitrile,
4-(4-cyano-3-{1-[(2,2-difluorocyclopropyl)methyl]-2-oxo-1,2-dihydro[1,3]thiazolo[5,4-b]pyridin-5-yl}phenoxy)pyridine-2-carbonitrile,
4-(4-cyano-3-{1-[(2,2-difluorocyclopropyl)methyl]-2-oxo-1,2-dihydro[1,3]thiazolo[5,4-b]pyridin-5-yl}phenoxy)pyridine-2-carbonitrile,
2-({3-[(2,2-difluorocyclopropyl)methyl]-2-oxo-2,3-dihydro-1,3-benzothiazol-6-yl}oxy)nicotinonitrile,
3-{[2,2-difluorocyclopropyl]methyl}-6-[(3,5-difluoropyridin-2-yl)oxy]-1,3-benzothiazol-2(3H)-one,
3-{[2,2-difluorocyclopropyl]methyl}-6-[(5-methylpyridin-2-yl)oxy]-1,3-benzothiazol-2(3H)-one,
2-[(3-{[2,2-difluorocyclopropyl]methyl}-2-oxo-2,3-dihydro-1,3-benzothiazol-6-yl)oxy]benzonitrile,
6-[(3-acetylpyridin-2-yl)oxy]-3-{[2,2-difluorocyclopropyl]methyl}-1,3-benzothiazol-2(3H)-one,
3-{[2,2-difluorocyclopropyl]methyl}-6-(pyridin-2-yloxy)-1,3-benzothiazol-2(3H)-one,
6-[(3-{[2,2-difluorocyclopropyl]methyl}-2-oxo-2,3-dihydro-1,3-benzothiazol-6-yl)oxy]pyridine-3-carbonitrile,
2-[(3-{[2,2-difluorocyclopropyl]methyl}-2-oxo-2,3-dihydro-1,3-benzothiazol-6-yl)oxy]pyridine-3-carbonitrile,
2-[(3-{[2,2-difluorocyclopropyl]methyl}-2-oxo-2,3-dihydro-1,3-benzothiazol-6-yl)oxy]-3-fluorobenzonitrile,
3-[(2,2-difluorocyclopropyl)methyl]-6-{[3-(1-hydroxyethyl)pyridin-2-yl]oxy}-1,3-benzothiazol-2(3H)-one,
or a pharmaceutically acceptable salt thereof.

12. The compound according to claim 11 which is:
2-(1-{[2,2-difluorocyclopropyl]methyl}-2-oxo-1,2-dihydro[1,3]thiazolo[5,4-b]pyridin-5-yl)benzonitrile;
2-[1-(2,2-dimethylpropyl)-2-oxo-1,2-dihydro[1,3]thiazolo[5,4-b]pyridin-5-yl]benzonitrile;
2-(3-{[2,2-difluorocyclopropyl]methyl}-2-oxo-2,3-dihydro-1,3-benzothiazol-6-yl)benzonitrile;
3-[(2,2-difluorocyclopropyl)methyl]-6-{[3-(1-hydroxyethyl)pyridin-2-yl]oxy}-1,3-benzothiazol-2(3H)-one;
3-{[2,2-difluorocyclopropyl]methyl}-6-[3-(1,1-dioxidothiomorpholin-4-yl)phenyl]-1,3-benzothiazol-2(3H)-one;
2-(3-{[2,2-difluorocyclopropyl]methyl}-2-oxo-2,3-dihydro-1,3-benzothiazol-6-yl)-4-(morpholin-4-ylmethyl)benzonitrile;
or a pharmaceutically acceptable salt thereof.

13. A pharmaceutical composition comprising a compound according to claim 1 in combination with a pharmaceutically acceptable carrier.

14. A method for treating schizophrenia in a patient in need thereof comprising administering to the patient a therapeutically effective amount of a compound according to claim 1, or a pharmaceutically acceptable salt thereof.

* * * * *